United States Patent
Colvin, Jr. et al.

(10) Patent No.: US 9,414,775 B2
(45) Date of Patent: *Aug. 16, 2016

(54) PURIFICATION OF GLUCOSE CONCENTRATION SIGNAL IN AN IMPLANTABLE FLUORESCENCE BASED GLUCOSE SENSOR

(71) Applicant: Senseonics, Incorporated, Germantown, MD (US)

(72) Inventors: Arthur E. Colvin, Jr., Mt. Airy, MD (US); Xiaolin Wang, Germantown, MD (US); Colleen Mdingi, Germantown, MD (US); Andrew DeHennis, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/937,871

(22) Filed: Jul. 9, 2013

(65) Prior Publication Data

US 2014/0018644 A1    Jan. 16, 2014

Related U.S. Application Data

(63) Continuation-in-part of application No. 13/853,095, filed on Mar. 29, 2013.

(60) Provisional application No. 61/617,414, filed on Mar. 29, 2012.

(51) Int. Cl.
*A61B 5/1455* (2006.01)
*A61B 5/145* (2006.01)
(Continued)

(52) U.S. Cl.
CPC .......... *A61B 5/14532* (2013.01); *A61B 5/1459* (2013.01); *A61B 5/14556* (2013.01); *A61B 5/7203* (2013.01)

(58) Field of Classification Search
USPC ................................................. 600/310–344
See application file for complete search history.

(56) References Cited

U.S. PATENT DOCUMENTS 5,873,990 A     2/1999   Wojciechowski et al.
6,330,464 B1 *  12/2001  Colvin et al. ................. 600/316
(Continued)

FOREIGN PATENT DOCUMENTS

WO       03-025562 A2     3/2003
WO       2010/033901 A1   3/2010
WO       2010/141888 A1   12/2010

*Primary Examiner* — Eric Winakur
*Assistant Examiner* — Marjan Fardanesh
(74) *Attorney, Agent, or Firm* — Rothwell, Figg, Ernst & Manbeck, P.C.

(57) ABSTRACT

Methods, sensors, and systems for determining a concentration of glucose in a medium of a living animal are disclosed. Determining the glucose concentration may involve emitting excitation light from a light source to indicator molecules, generating a raw signal indicative of the amount of light received by a photodetector, purifying and normalizing the raw signal, and converting the normalized signal to a glucose concentration. The purification may involve removing noise (e.g., offset and/or distortion) from the raw signal. The purification and normalization may involve tracking the cumulative emission time that the light source has emitted the excitation light and tracking the implant time that has elapsed since the optical sensor was implanted. The purification and normalization may involve measuring the temperature of the sensor. The purification, normalization, and conversion may involve using parameters determined during manufacturing, in vitro testing, and/or in vivo testing.

32 Claims, 9 Drawing Sheets

(51) Int. Cl.
*A61B 5/1459* (2006.01)
*A61B 5/00* (2006.01)

(56) References Cited

U.S. PATENT DOCUMENTS

| | | |
|---|---|---|
| 2002/0128546 A1 | 9/2002 | Silver |
| 2005/0236580 A1 | 10/2005 | Colvin, Jr. et al. |
| 2007/0014726 A1 | 1/2007 | Merical et al. |
| 2007/0043280 A1* | 2/2007 | Mannheimer et al. ........ 600/331 |
| 2008/0108885 A1 | 5/2008 | Colvin, Jr. |
| 2008/0188725 A1* | 8/2008 | Markle et al. ................. 600/316 |
| 2009/0036760 A1* | 2/2009 | Hayter ........................... 600/316 |
| 2009/0192745 A1 | 7/2009 | Kamath et al. |
| 2010/0024526 A1 | 2/2010 | Colvin, Jr. et al. |
| 2010/0196918 A1 | 8/2010 | Ellis et al. |

* cited by examiner

PURIFICATION OF GLUCOSE CONCENTRATION SIGNAL IN AN IMPLANTABLE FLUORESCENCE BASED GLUCOSE SENSOR

CROSS-REFERENCE TO RELATED APPLICATION

The present application is a continuation-in-part of U.S. patent application Ser. No. 13/853,095, filed on Mar. 29, 2013, which is incorporated by reference in its entirety and claims the benefit of priority to U.S. Provisional Application Ser. No. 61/617,414, filed on Mar. 29, 2012, which is also incorporated herein by reference in its entirety.

BACKGROUND

1. Field of Invention

The present invention relates generally to determining a concentration of glucose in interstitial fluid of a living animal using an optical sensor implanted in the living animal. Specifically, the present invention relates to purification of a raw signal including a glucose-modulated component to remove noise (e.g., offset and/or distortion) and converting the processed signal to a glucose concentration.

2. Discussion of the Background

A sensor may be implanted within a living animal (e.g., a human) used to measure the concentration of glucose in a medium (e.g., interstitial fluid (ISF) or blood) within the living animal. The sensor may include a light source (e.g., a light-emitting diode (LED) or other light emitting element), indicator molecules, and a photodetector (e.g., a photodiode, phototransistor, photoresistor or other photosensitive element). Examples of implantable sensors employing indicator molecules to measure the concentration of an analyte are described in U.S. Pat. Nos. 5,517,313 and 5,512,246, which are incorporated herein by reference in their entirety.

Broadly speaking, in the context of the field of the present invention, indicator molecules are molecules having one or more optical characteristics that is or are affected by the local presence of an analyte such as glucose. The indicator molecules may be fluorescent indicator molecules, and the fluorescence of the indicator molecules may be modulated, i.e., attenuated or enhanced, by the local presence of glucose.

The implantable sensor may be configured such that fluorescent light emitted by the indicator molecules impacts the photodetector, which generates a raw electrical signal based on the amount of light received thereby. The generated raw electrical signal may be indicative of the concentration of glucose in the medium surrounding the indicator molecules, but the raw signal may also include noise (e.g., offset and/or distortion) that affects the accuracy of the glucose concentration measurement produced from the raw signal.

There is presently a need in the art for a more accurate sensor capable of measuring glucose concentration in a medium of a living animal.

SUMMARY

One aspect of the invention may provide a method of determining a concentration of glucose in a medium of a living animal using an optical sensor implanted in the living animal and a sensor reader external to the living animal. The method may include emitting, using a light source of the optical sensor, excitation light to indicator molecules of the optical sensor. The indicator molecules may have an optical characteristic responsive to the concentration of glucose. The method may include generating, using a photodetector of the optical sensor, a raw signal indicative of the amount of light received by the photodetector. The light received by the photodetector may include glucose-modulated light emitted by the indicator molecules and at least one of excitation light emitted by the light source and non-glucose modulated light emitted by the indicator molecules. The method may include conveying, using an inductive element of the optical sensor, the raw signal. The method may include receiving, using an inductive element of the sensor reader, the conveyed raw signal. The method may include tracking, using circuitry of the sensor reader, the cumulative emission time that the light source has emitted the excitation light. The method may include tracking, using circuitry of the sensor reader, the implant time that has elapsed since the optical sensor was implanted in the living animal. The method may include adjusting, using circuitry of the sensor reader, the received raw signal to compensate for offset and distortion based on the tracked cumulative emission time and the tracked implant time. The method may include converting, using circuitry of the sensor reader, the adjusted signal into a measurement of glucose concentration in the medium of the living animal.

Another aspect of the invention may provide a system for determining a concentration of glucose in a medium of a living animal. The system may include and optical sensor implanted in the living animal and a sensor external to the living animal. The optical sensor may include: indicator molecules, a light source, a photodetector, and an inductive element. The indicator molecules may have an optical characteristic responsive to the concentration of glucose. The light source may be configured to emit excitation light to the indicator molecules. The photodetector may be configured to generate a raw signal indicative of the amount of light received by the photodetector. The light received by the photodetector may include glucose-modulated light emitted by the indicator molecules and at least one of excitation light emitted by the light source and non-glucose modulated light emitted by the indicator molecules. The inductive element may be configured to convey the raw signal. The sensor reader may include an inductive element and circuitry. The inductive element may be configured to receive the conveyed raw signal. The circuitry may be configured to: track the cumulative emission time that the light source has emitted the excitation light; track the implant time that has elapsed since the optical sensor was implanted in the living animal; adjust the received raw signal to compensate for offset and distortion based on the tracked cumulative emission time and the tracked implant time; and convert the adjusted signal into a measurement of glucose concentration in the medium of the living animal.

Another aspect of the invention may provide a method of determining a concentration of glucose in a medium of a living animal using an optical sensor implanted in the living animal and a sensor reader external to the living animal. The method may include emitting, using a light source of the optical sensor, excitation light to indicator molecules of the optical sensor. The indicator molecules may have an optical characteristic responsive to the concentration of glucose. The method may include generating, using a photodetector of the optical sensor, a raw signal indicative of the amount of light received by the photodetector. The light received by the photodetector may include glucose-modulated light emitted by the indicator molecules and at least one of excitation light emitted by the light source and non-glucose modulated light emitted by the indicator molecules. The method may include measuring, using a temperature sensor of the optical sensor, a temperature of the optical sensor. The method may include conveying, using an inductive element of the optical sensor, the raw signal and measured temperature. The method may include receiving, using an inductive element of the sensor reader, the conveyed raw signal and the conveyed temperature. The method may include tracking the cumulative emission time that the light source has emitted the excitation light. The method may include tracking the implant time that has elapsed since the optical sensor was implanted in the living animal. The method may include temperature correcting, using circuitry of the sensor reader, the received raw signal to compensate for temperature sensitivity of the light source based on the received measured temperature. The method may include offset adjusting, using the circuitry of the sensor reader, the temperature corrected raw signal to compensate for offset based on the tracked cumulative emission time. The method may include distortion adjusting, using the circuitry of the sensor reader, the offset adjusted raw signal to compensate for distortion based on the tracked cumulative emission time and the tracked implant time. The method may include normalizing, using the circuitry of the sensor reader, the distortion adjusted raw signal to a normalized raw signal that would be equal to one at zero glucose concentration based on the measured temperature, the tracked cumulative emission time, and the tracked implant time. The method may include converting, using the circuitry of the sensor reader, the normalized raw signal into a measurement of glucose concentration in the medium of the living animal.

Still another aspect of the invention may provide a method of determining a concentration of glucose in a medium of a living animal using an optical sensor implanted in the living animal and a sensor reader external to the living animal. The method may include emitting, using a light source of the optical sensor, excitation light to indicator molecules of the optical sensor. The indicator molecules may have an optical characteristic responsive to the concentration of glucose. The method may include generating, using a photodetector of the optical sensor, a raw signal indicative of the amount of light received by the photodetector. The light received by the photodetector may include glucose-modulated light emitted by the indicator molecules and at least one of excitation light emitted by the light source and non-glucose modulated light emitted by the indicator molecules. The method may include tracking the cumulative emission time that the light source has emitted the excitation light. The method may include tracking the implant time that has elapsed since the optical sensor was implanted in the living animal. The method may include adjusting the raw signal to compensate for offset and distortion based on the tracked cumulative emission time and the tracked implant time. The method may include converting the adjusted signal into a measurement of glucose concentration in the medium of the living animal.

Another aspect of the invention may provide a method of determining a concentration of glucose in a medium of a living animal using an optical sensor implanted in the living animal and a sensor reader external to the living animal. The method may include emitting, using a light source of the optical sensor, excitation light to indicator molecules of the optical sensor. The indicator molecules may have an optical characteristic responsive to the concentration of glucose. The method may include generating, using a photodetector of the optical sensor, a raw signal indicative of the amount of light received by the photodetector. The light received by the photodetector may include glucose-modulated light emitted by the indicator molecules and at least one of excitation light emitted by the light source and non-glucose modulated light emitted by the indicator molecules. The method may include measuring, using a temperature sensor of the optical sensor, a temperature of the optical sensor. The method may include tracking the cumulative emission time that the light source has emitted the excitation light. The method may include tracking the implant time that has elapsed since the optical sensor was implanted in the living animal. The method may include temperature correcting the raw signal to compensate for temperature sensitivity of the light source based on the measured temperature. The method may include offset adjusting the temperature corrected raw signal to compensate for offset based on the tracked cumulative emission time. The method may include distortion adjusting the offset adjusted raw signal to compensate for distortion based on the tracked cumulative emission time and the tracked implant time. The method may include normalizing the distortion adjusted raw signal to a normalized raw signal that would be equal to one at zero glucose concentration based on the measured temperature, the tracked cumulative emission time, and the tracked implant time. The method may include converting the normalized raw signal into a measurement of glucose concentration in the medium of the living animal.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF PREFERRED EMBODIMENTS

Figure 1:
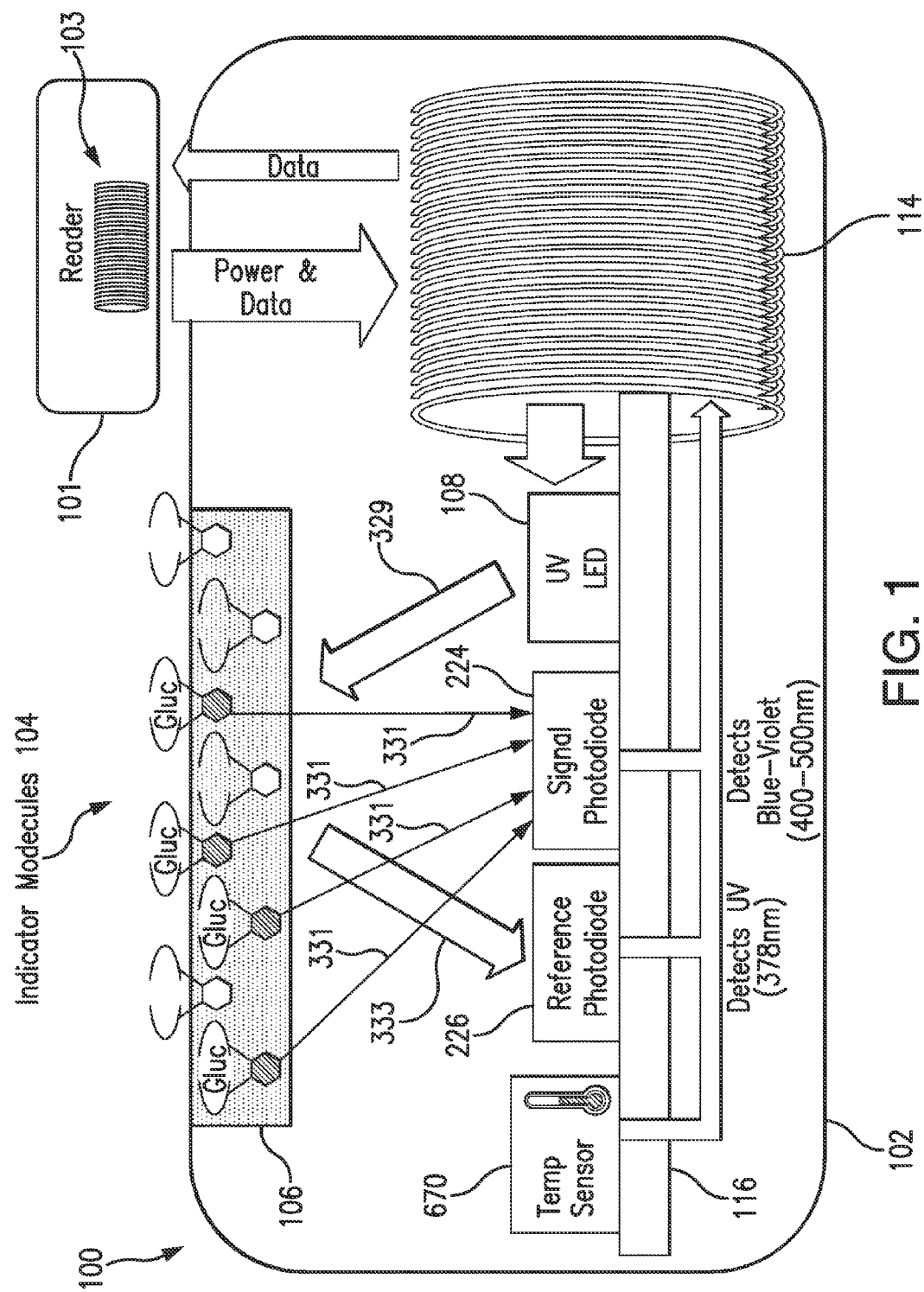
FIG. 1 is a schematic view illustrating a sensor system embodying aspects of the present invention.

FIG. 1 is a schematic view of a sensor system embodying aspects of the present invention. In one non-limiting embodiment, the system includes a sensor 100 and an external sensor reader 101. In the embodiment shown in FIG. 1, the sensor 100 may be implanted in a living animal (e.g., a living human). The sensor 100 may be implanted, for example, in a living animal's arm, wrist, leg, abdomen, or other region of the living animal suitable for sensor implantation. For example, in one non-limiting embodiment, the sensor 100 may be implanted between the skin and subcutaneous tissues. In some embodiments, the sensor 100 may be an optical sensor (e.g., a fluorometer). In some embodiments, the sensor 100 may be a chemical or biochemical sensor.

A sensor reader 101 may be an electronic device that communicates with the sensor 100 to power the sensor 100 and/or obtain analyte (e.g., glucose) readings from the sensor 100. In non-limiting embodiments, the reader 101 may be a handheld reader, a wristwatch, an armband, or other device placed in close proximity to the sensor 100. In one embodiment, positioning (i.e., hovering or swiping/waiving/passing) the reader 101 within range over the sensor implant site (i.e., within proximity of the sensor 100) will cause the reader 101 to automatically convey a measurement command to the sensor 100 and receive a reading from the sensor 100.

In some embodiments, the sensor reader 101 may include an inductive element 103, such as, for example, a coil. The sensor reader 101 may generate an electromagnetic wave or electrodynamic field (e.g., by using a coil) to induce a current in an inductive element 114 of the sensor 100, which powers the sensor 100. The sensor reader 101 may also convey data (e.g., commands) to the sensor 100. For example, in a non-limiting embodiment, the sensor reader 101 may convey data by modulating the electromagnetic wave used to power the sensor 100 (e.g., by modulating the current flowing through a coil 103 of the sensor reader 101). The modulation in the electromagnetic wave generated by the reader 101 may be detected/extracted by the sensor 100. Moreover, the sensor reader 101 may receive data (e.g., measurement information) from the sensor 100. For example, in a non-limiting embodiment, the sensor reader 101 may receive data by detecting modulations in the electromagnetic wave generated by the sensor 100, e.g., by detecting modulations in the current flowing through the coil 103 of the sensor reader 101.

The inductive element 103 of the sensor reader 101 and the inductive element 114 of the sensor 100 may be in any configuration that permits adequate field strength to be achieved when the two inductive elements are brought within adequate physical proximity.

Figure 9:
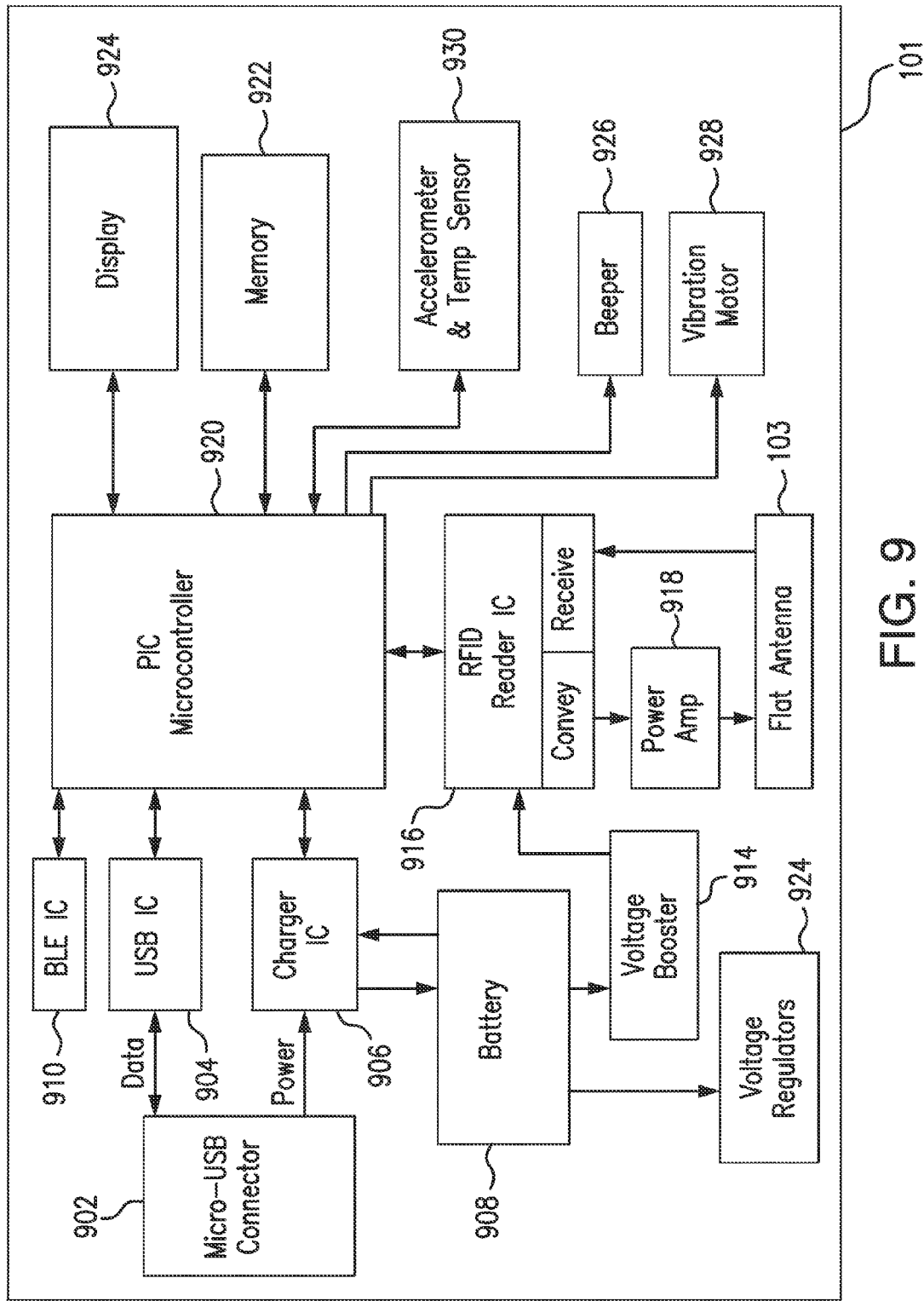
FIG. 9 is a schematic view illustrating a sensor reader embodying aspects of the present invention.

FIG. 9 is a schematic view of a sensor reader 101 according to a non-limiting embodiment. In some embodiments, the sensor reader 101 may have a connector 902, such as, for example, a Micro-Universal Serial Bus (USB) connector. The connector 902 may enable a wired connection to an external device, such as a personal computer or smart phone. The sensor reader 101 may exchange data to and from the external device through the connector 902 and/or may receive power through the connector 902. The sensor reader 101 may include a connector integrated circuit (IC) 904, such as, for example, a USB-IC, which may control transmission and receipt of data through the connector 902. The sensor reader 101 may also include a charger IC 906, which may receive power via the connector 902 and charge a battery 908.

In some embodiments, the sensor reader 101 may have a wireless communication IC 910, which enables wireless communication with an external device, such as, for example, a personal computer or smart phone. In one non-limiting embodiment, the communication IC 910 may employ a standard, such as, for example, a Buetooth Low Energy (BLE) standard (e.g., BLE 4.0), to wirelessly transmit and receive data to and from an external device.

In some embodiments, the sensor reader 101 may include voltage regulators 912 and/or a voltage booster 914. The battery 908 may supply power (via voltage booster 914) to radio-frequency identification (RFID) reader IC 916, which uses the inductive element 103 to convey information (e.g., commands) to the sensor 101 and receive information (e.g., measurement information) from the sensor 100. In the illustrated embodiment, the inductive element is a flat antenna. However, as noted above, the inductive element 103 of the sensor reader 101 may be in any configuration that permits adequate field strength to be achieved when brought within adequate physical proximity to the inductive element 114 of the sensor 100. In some embodiments, the sensor reader 101 may include a power amplifier 918 to amplify the signal to be conveyed by the inductive element 103 to the sensor 100.

The sensor reader 101 may include a peripheral interface controller (PIC) microcontroller 920 and memory 922 (e.g., Flash memory), which may be non-volatile and/or capable of being electronically erased and/or rewritten. The PIC microcontroller 920 may control the overall operation of the sensor reader 101. For example, the PIC microcontroller 920 may control the connector IC 904 or wireless communication IC 910 to transmit data and/or control the RFID reader IC 916 to convey data via the inductive element 103. The PIC microcontroller 920 may also control processing of data received via the inductive element 103, connector 902, or wireless communication IC 910.

In some embodiments, the sensor reader 101 may include a display 924 (e.g., liquid crystal display), which PIC microcontroller 920 may control to display data (e.g., glucose concentration values). In some embodiments, the sensor reader 101 may include a speaker 926 (e.g., a beeper) and/or vibration motor 928, which may be activated, for example, in the event that an alarm condition (e.g., detection of a hypoglycemic or hyperglycemic condition) is met. The sensor reader 101 may also include one or more additional sensors 930, which may include an accelerometer and/or temperature sensor, that may be used in the processing performed by the PIC microcontroller 920.

In one non-limiting embodiment, as illustrated in FIG. 1, sensor 100 includes a sensor housing 102 (i.e., body, shell, capsule, or encasement), which may be rigid and biocompatible. In exemplary embodiments, sensor housing 102 may be formed from a suitable, optically transmissive polymer material, such as, for example, acrylic polymers (e.g., polymethylmethacrylate (PMMA)).

In some embodiments, the sensor 100 includes indicator molecules 104. Indicator molecules 104 may be fluorescent indicator molecules (e.g., Trimethyltrifluromethylsilane (TFM) fluorescent indicator molecules) or absorption indicator molecules. In some embodiments, the indicator molecules 104 may reversibly bind glucose. When an indicator molecule 104 has bound glucose, the indicator molecule may become fluorescent, in which case the indicator molecule 104 is capable of absorbing (or being excited by) excitation light 329 and emitting light 331. In one non-limiting embodiment, the excitation light 329 may have a wavelength of approximately 378 nm, and the emission light 331 may have a wavelength in the range of 400 to 500 nm. When no glucose is bound, the indicator molecule 104 may be only weakly fluorescent.

In some non-limiting embodiments, sensor 100 may include a polymer graft 106 coated, diffused, adhered, or embedded on at least a portion of the exterior surface of the sensor housing 102, with the indicator molecules 104 distributed throughout the polymer graft 106. In some embodiments, the polymer graft 106 may be a fluorescent glucose indicating polymer. In one non-limiting embodiment, the polymer is biocompatible and stable, grafted onto the surface of sensor housing 102, designed to allow for the direct measurement of interstitial fluid (ISF) glucose after subcutaneous implantation of the sensor 100.

In some non-limiting embodiments, the polymer graft 106 may include three monomers: the TFM fluorescent indicator, hydroxyethylmethacrylate (HEMA), and polyethylene glycol methacrylate (PEG-methacrylate). In one embodiment, the polymer graft 106 may include the three monomers in specific molar ratios, with the fluorescent indicator comprising 0.1 molar percent, HEMA comprising 94.3 molar percent, and PEG-methacrylate comprising 5.6 molar percent. The PEG-methacrylate may act as a cross-linker and be what creates a sponge-like matrix. Conventional free radical polymerization may be used to synthesize the polymer that is grafted onto the sensor 100.

In some embodiments, the sensor 100 may include a light source 108, which may be, for example, a light emitting diode (LED) or other light source, that emits radiation, including radiation over a range of wavelengths that interact with the indicator molecules 104. In other words, the light source 108 may emit the excitation light 329 that is absorbed by the indicator molecules in the matrix layer/polymer 104. As noted above, in one non-limiting embodiment, the light source 108 may emit excitation light 329 at a wavelength of approximately 378 nm.

In some embodiments, the sensor 100 may also include one or more photodetectors (e.g., photodiodes, phototransistors, photoresistors or other photosensitive elements). For example, in the embodiment illustrated in FIG. 1, sensor 100 has a first photodetector 224 and a second photodetector 226. However, this is not required, and, in some alternative embodiments, the sensor 100 may only include the first photodetector 224.

Some part of the excitation light 329 emitted by the light source 108 may be reflected from the polymer graft 106 back into the sensor 100 as reflection light 331, and some part of the absorbed excitation light may be emitted as emitted (fluoresced) light 331. In one non-limiting embodiment, the emitted light 331 may have a higher wavelength than the wavelength of the excitation light 329. The reflected light 333 and emitted (fluoresced) light 331 may be absorbed by the one or more photodetectors (e.g., first and second photodetectors 224 and 226) within the body of the sensor 100.

Each of the one or more photodetectors may be covered by a filter 112 (see FIG. 3) that allows only a certain subset of wavelengths of light to pass through. In some embodiments, the one or more filters 112 may be thin glass filters. In some embodiments, the one or more filters 112 may be thin film (dichroic) filters deposited on the glass and may pass only a narrow band of wavelengths and otherwise reflect most of the light. In one non-limiting embodiment, the second (reference) photodetector 226 may be covered by a reference photodiode filter that passes light at the same wavelength as is emitted from the light source 108 (e.g., 378 nm). The first (signal) photodetector 224 may detect the amount of fluoresced light 331 that is emitted from the molecules 104 in the graft 106. In one non-limiting embodiment, the peak emission of the indicator molecules 104 may occur around 435 nm, and the first photodetector 224 may be covered by a signal filter that passes light in the range of about 400 nm to 500 nm. In some embodiments, higher glucose levels/concentrations correspond to a greater amount of fluorescence of the molecules 104 in the graft 106, and, therefore, a greater number of photons striking the first photodetector 224.

In some embodiments, sensor 100 may include a substrate 116. In some non-limiting embodiments, the substrate 116 may be a semiconductor substrate and circuitry may be fabricated in the semiconductor substrate 116. The circuitry may include analog and/or digital circuitry. Also, although in some preferred embodiments the circuitry is fabricated in the semiconductor substrate 116, in alternative embodiments, a portion or all of the circuitry may be mounted or otherwise attached to the semiconductor substrate 116. In other words, in alternative embodiments, a portion or all of the circuitry, which may include discrete circuit elements, an integrated circuit (e.g., an application specific integrated circuit (ASIC)) and/or other electronic components, may be fabricated in the semiconductor substrate 116 with the remainder of the circuitry is secured to the semiconductor substrate 116, which may provide communication paths between the various secured components. In some embodiments, circuitry of the sensor 100 may have the structure described in U.S. patent application Ser. No. 13/650,016, which is incorporated herein by reference in its entirety, with reference to FIG. 11D.

Figure 6:
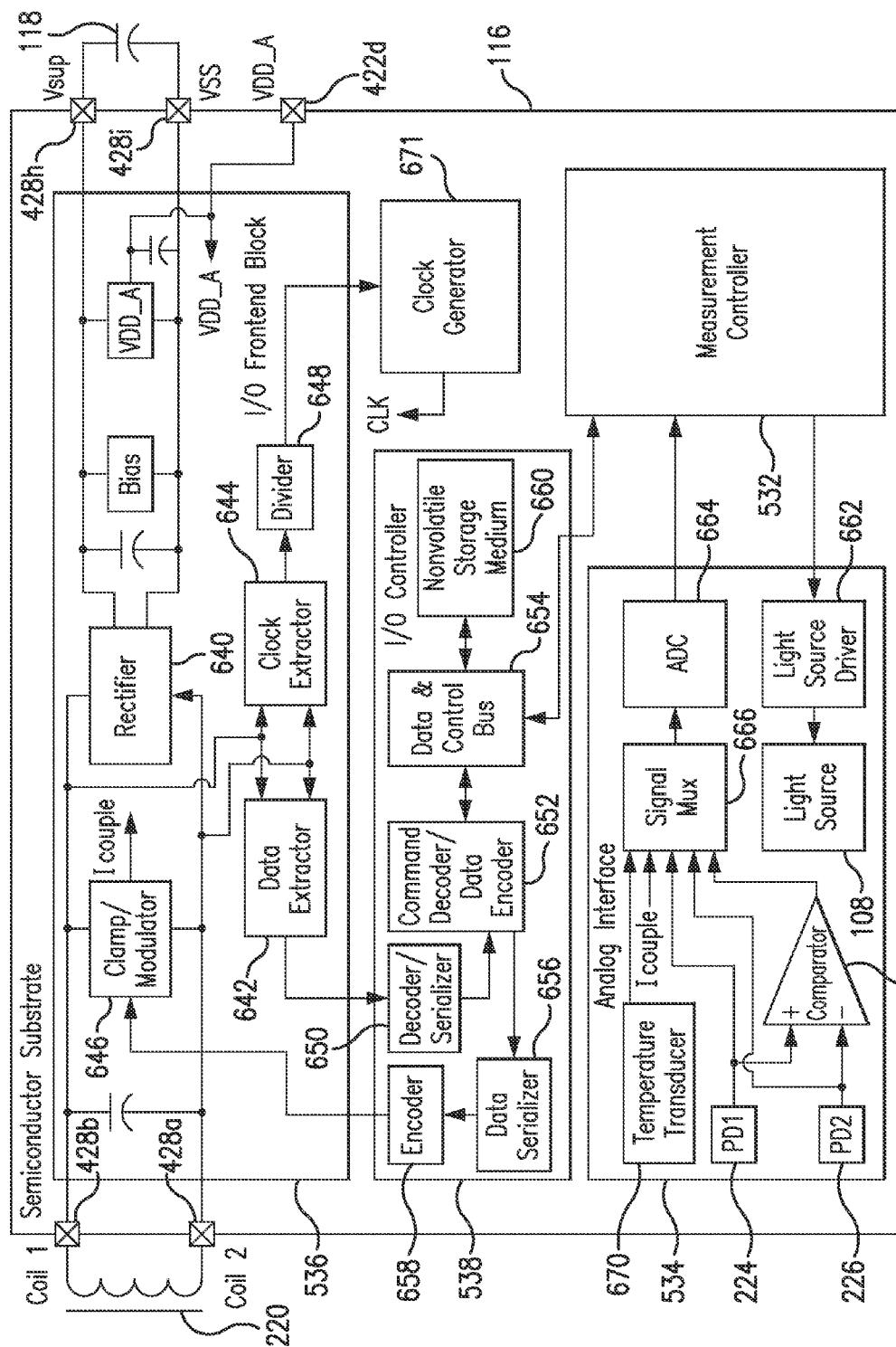
FIG. 6 illustrates a circuit diagram that may be used in accordance with one embodiment of the present invention.

FIG. 6 is block diagram illustrating the functional blocks of the circuitry of sensor 100 according to a non-limiting embodiment in which the circuitry is fabricated in the semiconductor substrate 116. As shown in the embodiment of FIG. 6, in some embodiments, an input/output (I/O) frontend block 536 may be connected to the external inductive element 114, which may be in the form of a coil 220, through coil contacts 428a and 428b. The I/O frontend block 536 may include a rectifier 640, a data extractor 642, a clock extractor 644, clamp/modulator 646 and/or frequency divider 648. Data extractor 642, clock extractor 644 and clamp/modulator 646 may each be connected to external coil 220 through coil contacts 428a and 428b. The rectifier 640 may convert an alternating current produced by coil 220 to a direct current that may be used to power the sensor 100. For instance, the direct current may be used to produce one or more voltages, such as, for example, voltage VDD_A, which may be used to power the one or more photodetectors (e.g., photodetectors 224 and 226). In one non-limiting embodiment, the rectifier 640 may be a Schottky diode; however, other types of rectifiers may be used in other embodiments. The data extractor 642 may extract data from the alternating current produced by coil 220. The clock extractor 644 may extract a signal having a frequency (e.g., 13.56 MHz) from the alternating current produced by coil 220. The frequency divider 648 may divide the frequency of the signal output by the clock extractor 644. For example, in a non-limiting embodiment, the frequency divider 648 may be a 4:1 frequency divider that receives a signal having a frequency (e.g., 13.56 MHz) as an input and outputs a signal having a frequency (e.g., 3.39 MHz) equal to one fourth the frequency of the input signal. The outputs of rectifier 640 may be connected to one or more external capacitors 118 (e.g., one or more regulation capacitors) through contacts 428h and 428i.

In some embodiments, an I/O controller 538 may include a decoder/serializer 650, command decoder/data encoder 652, data and control bus 654, data serializer 656 and/or encoder 658. The decoder/serializer 650 may decode and serialize the data extracted by the data extractor 642 from the alternating current produced by coil 220. The command decoder/data encoder 652 may receive the data decoded and serialized by the decoder/serializer 650 and may decode commands therefrom. The data and control bus 654 may receive commands decoded by the command decoder/data encoder 652 and transfer the decoded commands to the measurement controller 532. The data and control bus 654 may also receive data, such as measurement information, from the measurement controller 532 and may transfer the received data to the command decoder/data encoder 652. The command decoder/data encoder 652 may encode the data received from the data and control bus 654. The data serializer 656 may receive encoded data from the command decoder/data encoder 652 and may serialize the received encoded data. The encoder 658 may receive serialized data from the data serializer 656 and may encode the serialized data. In a non-limiting embodiment, the encoder 658 may be a Manchester encoder that applies Manchester encoding (i.e., phase encoding) to the serialized data. However, in other embodiments, other types of encoders may alternatively be used for the encoder 658, such as, for example, an encoder that applies 8B/10B encoding to the serialized data.

The clamp/modulator 646 of the I/O frontend block 536 may receive the data encoded by the encoder 658 and may modulate the current flowing through the inductive element 114 (e.g., coil 220) as a function of the encoded data. In this way, the encoded data may be conveyed wirelessly by the inductive element 114 as a modulated electromagnetic wave. The conveyed data may be detected by an external reading device by, for example, measuring the current induced by the modulated electromagnetic wave in a coil of the external reading device. Furthermore, by modulating the current flowing through the coil 220 as a function of the encoded data, the encoded data may be conveyed wirelessly by the coil 220 as a modulated electromagnetic wave even while the coil 220 is being used to produce operating power for the sensor 100. See, for example, U.S. Pat. Nos. 6,330,464 and 8,073,548, which are incorporated herein by reference in their entireties and which describe a coil used to provide operative power to an optical sensor and to wirelessly convey data from the optical sensor. In some embodiments, the encoded data is conveyed by the sensor 100 using the clamp/modulator 646 at times when data (e.g., commands) are not being received by the sensor 100 and extracted by the data extractor 642. For example, in one non-limiting embodiment, all commands may be initiated by an external sensor reader (e.g., reader 101 of FIG. 1) and then responded to by the sensor 100 (e.g., after or as part of executing the command). In some embodiments, the communications received by the inductive element 114 and/or the communications conveyed by the inductive element 114 may be radio frequency (RF) communications. Although, in the illustrated embodiments, the sensor 100 includes a single coil 220, alternative embodiments of the sensor 100 may include two or more coils (e.g., one coil for data transmission and one coil for power and data reception).

In an embodiment, the I/O controller 538 may also include a nonvolatile storage medium 660. In a non-limiting embodiment, the nonvolatile storage medium 660 may be an electrically erasable programmable read only memory (EEPROM). However, in other embodiments, other types of nonvolatile storage media, such as flash memory, may be used. The nonvolatile storage medium 660 may receive write data (i.e., data to be written to the nonvolatile storage medium 660) from the data and control bus 654 and may supply read data (i.e., data read from the nonvolatile storage medium 660) to the data and control bus 654. In some embodiments, the nonvolatile storage medium 660 may have an integrated charge pump and/or may be connected to an external charge pump. In some embodiments, the nonvolatile storage medium 660 may store identification information (i.e., traceability or tracking information), measurement information and/or setup parameters (i.e., calibration information). In one embodiment, the identification information may uniquely identify the sensor 100. The unique identification information may, for example, enable full traceability of the sensor 100 through its production and subsequent use. In one embodiment, the nonvolatile storage medium 660 may store calibration information for each of the various sensor measurements.

In some embodiments, the analog interface 534 may include a light source driver 662, analog to digital converter (ADC) 664, a signal multiplexer (MUX) 666 and/or comparator 668. In a non-limiting embodiment, the comparator 668 may be a transimpedance amplifier, in other embodiments, different comparators may be used. The analog interface 534 may also include light source 108, one or more photodetectors (e.g., first and second photodetectors 224 and 226), and/or a temperature sensor 670 (e.g., temperature transducer).

In some embodiments, the one or more photodetectors (e.g., photodetectors 224 and 226) may be mounted on the semiconductor substrate 116, but, in some preferred embodiments, the one or more photodetectors 110 may be fabricated in the semiconductor substrate 116. In some embodiments, the light source 108 may be mounted on the semiconductor substrate 116. For example, in a non-limiting embodiment, the light source 108 may be flip-chip mounted on the semiconductor substrate 116. However, in some embodiments, the light source 108 may be fabricated in the semiconductor substrate 116.

In a non-limiting, exemplary embodiment, the temperature transducer 670 may be a band-gap based temperature transducer. However, in alternative embodiments, different types of temperature transducers may be used, such as, for example, thermistors or resistance temperature detectors. Furthermore, like the light source 108 and one or more photodetectors, in one or more alternative embodiments, the temperature transducer 670 may be mounted on semiconductor substrate 116 instead of being fabricated in semiconductor substrate 116.

The light source driver 662 may receive a signal from the measurement controller 532 indicating the light source current at which the light source 108 is to be driven, and the light source driver 662 may drive the light source 108 accordingly. The light source 108 may emit radiation from an emission point in accordance with a drive signal from the light source driver 662. The radiation may excite indicator molecules 104 distributed throughout the graft 106. The one or more photodetectors (e.g., first and second photodetectors 224 and 226) may each output an analog light measurement signal indicative of the amount of light received by the photodetector. For instance, in the embodiment illustrated in FIG. 6, the first photodetector 224 may output a first analog light measurement signal indicative of the amount of light received by the first photodetector 224, and the second photodetector 226 may output a first analog light measurement signal indicative of the amount of light received by the second photodetector 226. The comparator 668 may receive the first and second analog light measurement signals from the first and second photodetectors 224 and 226, respectively, and output an analog light difference measurement signal indicative of the difference between the first and second analog light measurement signals. The temperature transducer 670 may output an analog temperature measurement signal indicative of the temperature of the sensor 100. The signal MUX 666 may select one of the analog temperature measurement signal, the first analog light measurement signal, the second analog light measurement signal and the analog light difference measurement signal and may output the selected signal to the ADC 664. The ADC 664 may convert the selected analog signal received from the signal MUX 666 to a digital signal and supply the digital signal to the measurement controller 532. In this way, the ADC 664 may convert the analog temperature measurement signal, the first analog light measurement signal, the second analog light measurement signal, and the analog light difference measurement signal to a digital temperature measurement signal, a first digital light measurement signal, a second digital light measurement signal, and a digital light difference measurement signal, respectively, and may supply the digital signals, one at a time, to the measurement controller 532.

In some embodiments, the measurement controller 532 may receive one or more digital measurements and generate measurement information, which may be indicative of the presence and/or concentration of an analyte (e.g., glucose) in a medium in which the sensor 100 is implanted. In some embodiments, the generation of the measurement information may include conversion of a digitized raw signal (e.g., the first digital light measurement signal) into a glucose concentration. For accurate conversion, the measurement controller 532 may take into consideration the optics, electronics, and chemistry of the sensor 100. Further, in some embodiments, the measurement controller 532 may be used to obtain a purified signal of glucose concentration by eliminating noise (e.g., offset and distortions) that is present in the raw signals (e.g., the first digital light measurement signals).

In some embodiments, the circuitry of sensor 100 fabricated in the semiconductor substrate 116 may additionally include a clock generator 671. The clock generator 671 may receive, as an input, the output of the frequency divider 648 and generate a clock signal CLK. The clock signal CLK may be used by one or more components of one or more of the I/O frontend block 536, I/O controller 538, measurement controller 532, and analog interface 534.

In a non-limiting embodiment, data (e.g., decoded commands from the command decoder/data encoder 652 and/or read data from the nonvolatile storage medium 660) may be transferred from the data and control bus 654 of the I/O controller 538 to the measurement controller 532 via transfer registers and/or data (e.g., write data and/or measurement information) may be transferred from the measurement controller 532 to the data and control bus 654 of the I/O controller 538 via the transfer registers.

In some embodiments, the circuitry of sensor 100 may include a field strength measurement circuit. In embodiments, the field strength measurement circuit may be part of the I/O front end block 536, I/O controller 538, or the measurement controller 532 or may be a separate functional component. The field strength measurement circuit may measure the received (i.e., coupled) power (e.g., in mWatts). The field strength measurement circuit of the sensor 100 may produce a coupling value proportional to the strength of coupling between the inductive element 114 (e.g., coil 220) of the sensor 100 and the inductive element of the external reader 101. For example, in non-limiting embodiments, the coupling value may be a current or frequency proportional to the strength of coupling. In some embodiments, the field strength measurement circuit may additionally determine whether the strength of coupling/received power is sufficient to perform an analyte concentration measurement and convey the results thereof to the external sensor reader 101. For example, in some non-limiting embodiments, the field strength measurement circuit may detect whether the received power is sufficient to produce a certain voltage and/or current. In one non-limiting embodiment, the field strength measurement circuit may detect whether the received power produces a voltage of at least approximately 3V and a current of at least approximately 0.5 mA. However, other embodiments may detect that the received power produces at least a different voltage and/or at least a different current. In one non-limiting embodiment, the field strength measurement circuit may compare the coupling value field strength sufficiency threshold.

In the illustrated embodiment, the clamp/modulator 646 of the I/O circuit 536 acts as the field strength measurement circuit by providing a value (e.g., $I_{couple}$) proportional to the field strength. The field strength value $I_{couple}$ may be provided as an input to the signal MUX 666. When selected, the MUX 666 may output the field strength value $I_{couple}$ to the ADC 664. The ADC 664 may convert the field strength value $I_{couple}$ received from the signal MUX 666 to a digital field strength value signal and supply the digital field strength signal to the measurement controller 532. In this way, the field strength measurement may be made available to the measurement controller 532 and may be used in initiating an analyte measurement command trigger based on dynamic field alignment. However, in an alternative embodiment, the field strength measurement circuit may instead be an analog oscillator in the sensor 100 that sends a frequency corresponding to the voltage level on a rectifier 640 back to the reader 101.

In some embodiments, the sensor 100 may be used to obtain accurate ISF glucose readings in patients, and the circuitry of the sensor 100 (which may, for example, include measurement controller 532) may convert the raw signal generated by the photodetector 224 into a glucose concentration. For accurate conversion, the circuitry of the sensor 100 may take into consideration the optics, electronics, and chemistry of the sensor 100. Further, in some embodiments, the circuitry may be used to obtain a purified signal of glucose concentration by eliminating noise (e.g., offset and distortions) that are present in raw signals from the sensor 100.

In some embodiments, the circuitry may use parameters measured during manufacturing of the sensor 100 and parameters characterized as a result of in vitro and in vivo tests to convert the raw signals generated by the sensor 100 into glucose concentrations. In some embodiments, the intermediate steps performed by the circuitry of the sensor 100 in determining a glucose concentration from a raw signal may be: (i) purifying the raw signal, (ii) normalizing the purified signal to produce a normalized signal Sn that is directly proportional to glucose concentration, and (iii) converting the normalized signal Sn into a glucose concentration.

The purification may involve compensating for/removing impurities, such as an offset produced by the excitation light 329 and distortion produced by non-glucose modulated light emitted by the indicator molecules 104. In some embodiments, the purification may also involve correcting the raw signal for temperature sensitivity. Accordingly, the purified signal may be proportional to the glucose modulated indicator fluorescence emitted by the indicator molecules 104.

The raw signals from the sensor 100, as captured by the photodetector 224, may contain noise (e.g., offset and distortions), which are not related to actual glucose modulation of the indicator molecules 104. The fluorescent amplitude of the light 331 emitted by the indicator molecules 104, as well as some elements of the electronic circuitry within the sensor 100, may be temperature sensitive. The circuitry may, therefore, purify the raw signal by removing the non-glucose-modulated offset/distortion of the raw signal and correcting for temperature sensitivity before normalizing the signal and converting the normalized signal to a glucose concentration.

Figure 2:
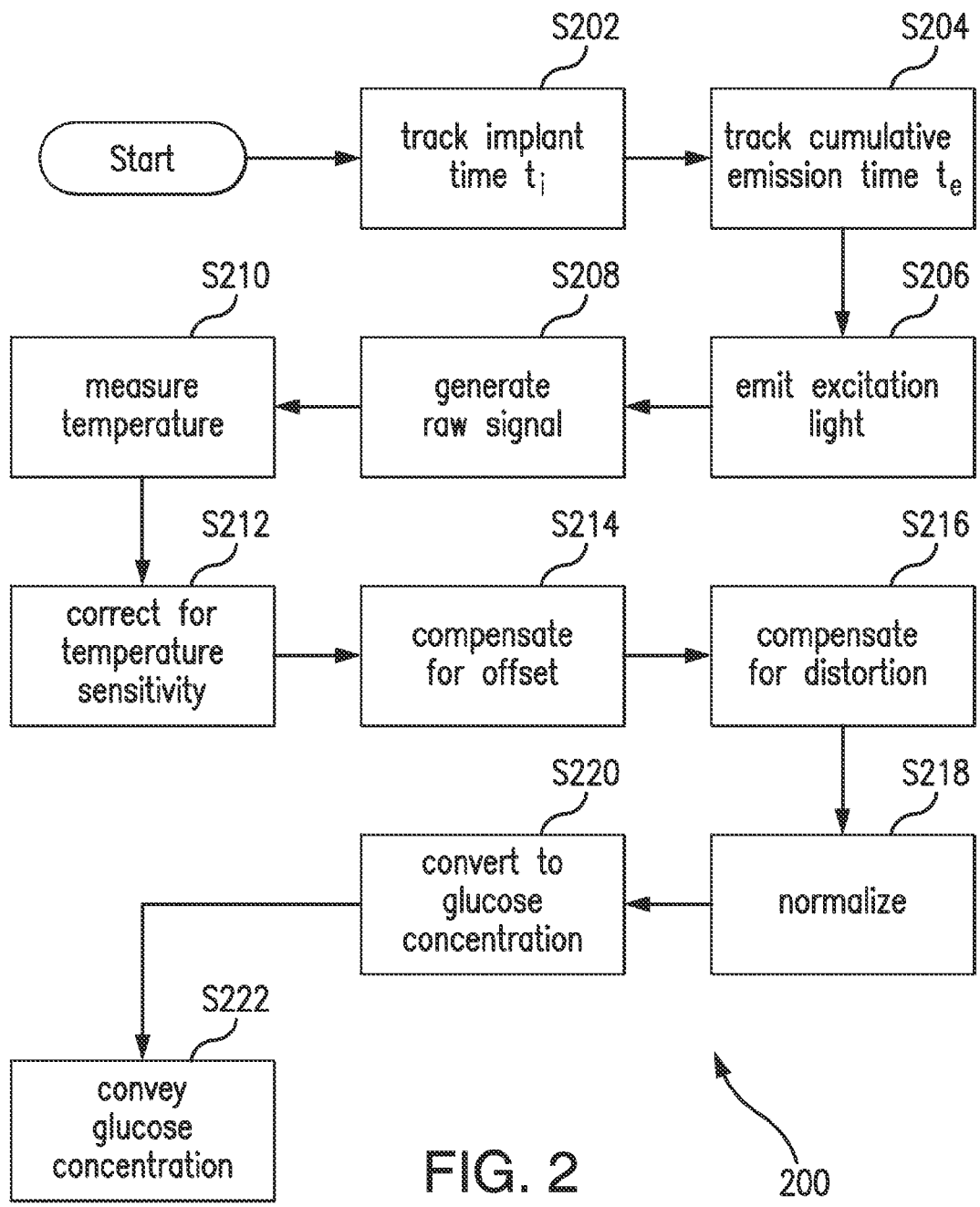
FIG. 2 illustrates a raw signal purification and conversion process that may be performed by the circuitry of an optical sensor in accordance with an embodiment of the present invention.

FIG. 2 illustrates an exemplary raw signal purification and conversion process 200 that may be performed by the circuitry of optical sensor 100, which may be, for example, implanted within a living animal (e.g., a living human), in accordance with an embodiment of the present invention. The process 200 may include a step S202 of tracking the amount of time $t_i$ that has elapsed since the optical sensor was implanted in the living animal. Because oxidation and thermal degradation begins when the sensor 100 is implanted, the implant time $t_i$ may be equivalent to the oxidation time $t_{ox}$ and the thermal degradation time $t_{th}$.

In some embodiments, the circuitry of sensor 100 may include an implant timer circuit that is started when the sensor is implanted. For example, in one non-limiting embodiment, the implant timer circuit may be a counter that increments with each passing of a unit of time (e.g., one or more milliseconds, one more seconds, one or more minutes, one or more hours, or one or more days, etc.). However, this is not required, and, in some alternative embodiments, the circuitry of the sensor 100 may track the implant time $t_i$ by storing the time at which the sensor was implanted (e.g., in nonvolatile storage medium 660) and comparing the stored time with the current time, which may, for example, be received from the external reader 101 (e.g., with an measurement command from the external reader 101). In other alternative embodiments, the sensor 100 may store the time at which the sensor was implanted, i.e., the implant time $t_i$ (e.g., in nonvolatile storage medium 660), which may then be read by an external unit (e.g., sensor reader 101) for calculation of the implant time $t_i$. As explained in detail below, the tracked implant time $t_i$ may be used in compensating for distortion in the raw signal, normalizing the raw signal, and/or converting the normalized signal Sn to a glucose concentration.

The process 200 may include a step S204 of tracking the cumulative amount of time $t_e$ that the light source 108 has emitted the excitation light 329. Because the indicator molecules 104 are irradiated with the excitation light 329, the cumulative emission time $t_e$ may be equivalent to the photobleaching time $t_{pb}$.

In some embodiments, the circuitry of sensor 100 includes an emission timer circuit that is advanced while the light source 108 emits excitation light 329. For example, in one non-limiting embodiment, the emission timer circuit may be a counter that increments with each passing of a unit of time (e.g., one or more milliseconds, one more seconds, one or more minutes, one or more hours, or one or more days, etc.) while the light source 108 emits excitation light 329. However, this is not required. For example, in some alternative embodiments, the light source 108 may emit excitation light 329 for a set amount of time for each measurement, and the counter may increment once for each measurement taken by the sensor 100. As explained in detail below, the tracked cumulative emission time $t_e$ may be used in compensating for offset in the raw signal, compensating for distortion in the raw signal, normalizing the raw signal, and/or converting the normalized signal Sn to a glucose concentration.

The process 200 may include a step S206 of emitting excitation light 329. The excitation light 329 may be emitted by light source 108. In some embodiments, step S206 may be carried out in response to a measurement command from the external sensor reader 101 (e.g., under the control of a measurement controller). Execution of step S206 may cause incrementing of the tracked cumulative emission time $t_e$, which may be equivalent to the photobleaching time $t_{pb}$.

The process 200 may include a step S208 of generating a raw signal indicative of the amount of light received by a photodetector (e.g., first photodetector 224). In some embodiments, the raw signal may be generated by the first (signal) photodetector 224. In some non-limiting embodiments, the raw signal may be digitized by the ADC 664.

As shown in equation 3, the raw signal may contain an offset Z and distortion $I_{distortion}$.

$$\text{Signal} = I + Z + I_{distortion} \quad (3)$$

where Signal is the raw signal generated by the photodetector, I is the glucose-modulated fluorescence from the indicator molecules 104, Z is an offset, and $I_{distortion}$ is distortion produced by the indicator molecules 104 (e.g., distortion produced by photo, thermal, and/or oxidative decay species of). In order to accurately calculate the glucose-modulated fluorescence I emitted by the indicator molecules 104, the raw signal may be purified by removing the offset Z and the distortion $I_{distortion}$ from the raw signal. In addition, for accurate calculation of the fluorescence from the glucose indicator I, the raw signal may be corrected for temperature sensitivity. Accordingly, the process 200 may include steps S210, S212, S214, and/or S216 of measuring temperature, correcting for temperature sensitivity, compensating for offset Z, and compensating for distortion $I_{distortion}$, respectively.

In step S210, the temperature T of the optical sensor 100 may be measured. In some embodiments, the temperature may be measured by the temperature sensor 670. As explained below, in some embodiments, the measured temperature T may be used for correcting the raw signal for temperature sensitivity.

In step S212, the circuitry of sensor 100 may temperature correct the raw signal based on the temperature T of the sensor 100, which may be measured in step S210. In particular, in some non-limiting embodiments, the measurement controller 532 may perform the temperature correction. As noted above, the fluorescent amplitude of the light 331 emitted by the indicator molecules 104, as well as some elements of the circuitry within the sensor 100 (e.g., light source 108), may be temperature sensitive. In one non-limiting embodiment, the circuitry (e.g., measurement controller 532) may correct for the temperature sensitivity as shown in equation 4:

$$[\text{Signal}]_T = \text{Signal}(1+(T-37)c_z) \quad (4)$$

wherein the Signal is the raw signal generated by the photodetector (e.g., photodetector 224), $[\text{Signal}]_T$ is the temperature corrected raw signal, and $c_z$ is the temperature sensitivity of the optical sensor. In one non-limiting embodiment, the temperature sensitivity may simply be the temperature sensitivity of the light source 108.

In step S214, the circuitry of sensor 100 may compensate for the offset Z present in the raw signal. In some embodiments, the offset Z may be hardware based. For example, in some embodiments, the offset Z may be related at least in part to the peak wavelength of the excitation light 329 emitted by the particular light source 108 used in sensor 100 and/or the tolerance of the particular optical band-pass filter 112 used in sensor 100.

The offset Z present in the raw signal may result from excitation light 329 emitted from light source 108 that reaches the photodetector (e.g., first (signal) photodetector 224). The excitation light 329 that reaches the photodetector is convoluted in the total light that reaches photodetector, and, thus, produces an offset in the raw signal generated by the photodetector.

Figure 3:
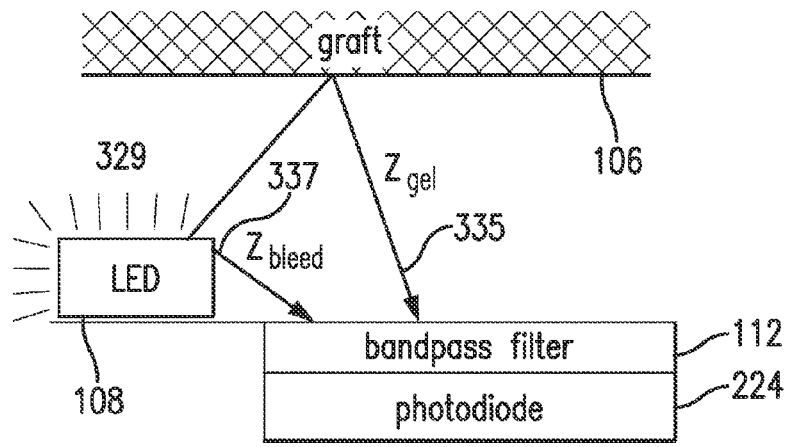
FIG. 3 illustrates the components of the excitation light received by the photodetector that contribute to the offset in the raw signal in accordance with an embodiment of the present invention.

As illustrated in FIG. 3, the excitation light 329 emitted from light source 108 that reaches the photodetector may include (i) a reflection light component 335 that is reflected from the graft 106 (e.g., gel) before reaching the photodetector and (ii) a bleed light component 337 that reaches the photodetector without encountering the graft 106. The reflection light component 335 may produce a reflection component $Z_{gel}$ of the offset Z, and the bleed light component 337 may produce a bleed component $Z_{bleed}$ of the offset Z.

In some embodiments, the offset Z may be measured during the manufacturing of the sensor 100. However, the offset Z may increase due to photobleaching of the indicator molecules 104. In particular, as indicator molecules 104 become photo-bleached, the overall absorbance of the graft/gel 106 decreases, which increases the reflectance of the graft/gel 106, the amount of excitation light 329 reflected from the graft/gel 106, and the intensity of the reflection light component 335. Accordingly, in some embodiments, in order to compensate for the offset in the raw signal, the circuitry of the sensor 100 may dynamically track the offset (e.g., by using the tracked cumulative emission time $t_e$).

In some embodiments, the circuitry of sensor 100 (e.g., measurement controller 532) may compensate for the offset Z present in the raw signal by calculating the offset Z and removing (e.g., subtracting) the offset Z from the raw signal. For example, in embodiments where the raw signal is temperature corrected, the calculated offset Z may be removed from the raw signal by subtracting the calculated offset Z from the temperature corrected raw signal $[Signal]_T$.

In one non-limiting embodiment, the circuitry of the sensor 100 (e.g., measurement controller 532) may calculate the offset Z as shown in equation 5:

$$[Z] = Z_{gel}(1+\phi_Z(1-e^{-k_{pb}t_{pb}})) + Z_{bleed} \quad (5)$$

where $Z_{gel}$ is the component of the offset Z produced by the reflection light component 335 (i.e., the excitation light 329 spillover component that is reflected from the graft 106 (e.g., gel) and received by the photodetector), $\phi_z$ is the percent increase of $Z_{gel}$ when the indicator is fully photo-bleached, $k_{pb}$ is the rate of photobleaching, $t_{pb}$ is the photobleaching time, and $Z_{bleed}$ is the component of the offset Z produced by the bleed light component 337 (i.e., the portion of the excitation light 329 received by the photodetector that reaches the photodetector without encountering the graft 106). In some embodiments, the circuitry (e.g., measurement controller 532) may use the tracked cumulative emission time $t_e$ for the photobleaching time $t_{pb}$.

Figure 4:
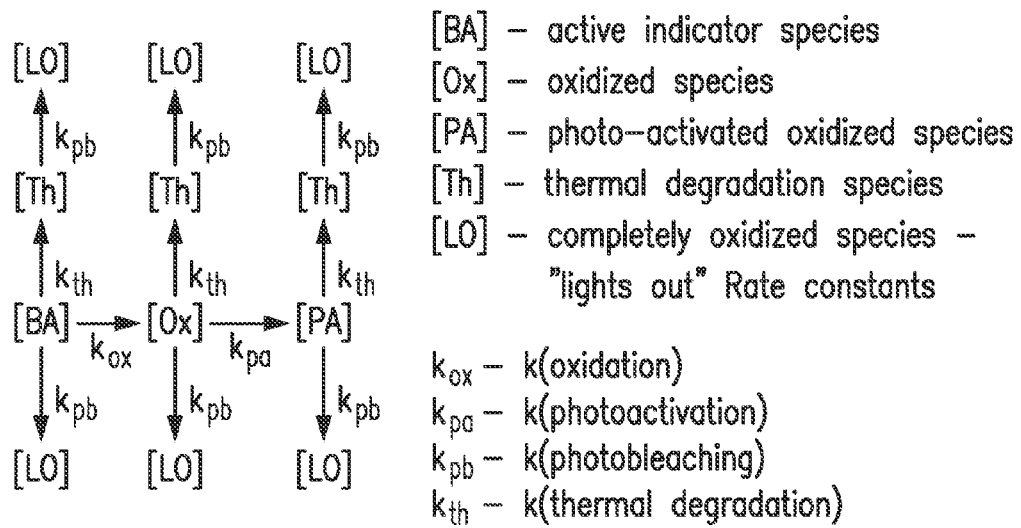
FIG. 4 illustrates the reactions and kinetics of the related species of the indicator molecules in accordance with an embodiment of the present invention.

In step S216, the circuitry of sensor 100 may compensate for the distortion $I_{distortion}$ present in the raw signal. In particular, in some embodiments, the measurement controller 532 may perform the distortion compensation. The distortion $I_{distortion}$ may be chemistry (photochemistry) and kinetics based. The distortion $I_{distortion}$ may be any non-glucose-modulated light in the emission light 331 arriving at the photodetector from the indicator molecules 104. For example, photo, thermal, and oxidative decay species of the indicator molecules 104 may emit fluorescent light that is not modulated by glucose. In fact, most of the distortion $I_{distortion}$ may be due to various matrix species kinetically related to the parent indicator BA (i.e., the active indicator species) as shown in FIG. 4.

In some embodiments, the glucose indicator molecule BA, within an in-vivo environment, may undergo a steady loss of signal amplitude over time. The glucose indicator molecule BA may be temperature sensitive. In some embodiments, oxidation, thermal degradation, and photobleaching may be the dominant mechanisms of the signal degradation. In some embodiments, the oxidation, thermal degradation, and photobleaching may all be chronic and predictable under a first order decay function on the loss of signal amplitude. This decay may establish the end of useful life for the overall sensor product. In some embodiments, the glucose indicator BA may be degraded by the three decay mechanisms (i.e., oxidation, thermal degradation, and photobleaching).

In regard to oxidative decay species Ox, in some non-limiting embodiments, under in-vivo conditions, oxidation pressure from ambient and normal reactive oxidation species (ROS), the glucose indicator BA may progressively undergo a highly specific oxidative de-boronation. This reaction may remove the boronate recognition moiety of the indicator molecule BA. The resulting deboronated indicator (i.e., oxidized indicator Ox) may be fluorescent (e.g., at a lower quantum efficiency than the glucose indicator BA) and may not modulate. Moreover, the oxidized species Ox may be temperature sensitive and may decay due to photo activation, photobleaching, and/or thermal degradation.

In regard to photo-activated decay species PA, when the oxidized indicator Ox is photo activated, it may produce a major product (i.e., photo-activated oxidated species PA). Photo-activated oxidated species PA may be fluorescent (e.g., at a higher quantum efficiency than oxidized species Ox) and may not modulate. Similar to the oxidized species Ox, the photo-activated oxidated species PA may be temperature sensitive and may decay due to photobleaching and/or thermal degradation.

In regard to thermal degradation product species Th, the glucose indicator BA, the oxidized indicator Ox, and the photo-activated decay species PA, may all thermally degrade. Similar to the oxidized species Ox and the photo-activated oxidated species PA, the resulting thermally degraded indicator Th may be fluorescent (e.g., at a lower quantum efficiency than the glucose indicator BA) and does not modulate. The thermal degradation product species Th may be temperature sensitive and may decay due to photobleaching.

The oxidated species Ox, photo-activated oxidated species PA, and thermal degradation product species Th illustrated in FIG. 4 are fluorescent derivatives of the base glucose-indicator BA. However, only the base glucose-indicator BA of the indicator molecules 104 is a glucose modulated species. Therefore, to obtain the most accurate measurement of glucose concentration based on the emission light 331 received by the photodetector, the fluorescence I produced by the base glucose-indicator BA, which carries glucose concentration information, may be de-convoluted from the emission light 331, which also include fluorescence from the oxidated species Ox, photo-activated oxidated species PA, and thermal degradation product species Th. In other words, the oxidated species Ox, photo-activated oxidated species PA, and thermal degradation product species Th are distortion-producing species, and the non-glucose-modulated light $I_{distortion}$ from these species may be removed from the raw signal. Accordingly, the circuitry of the sensor 100 may track each of the distortion-producing species and remove them from the final signal that is converted to a glucose concentration measurement.

As shown in FIG. 4, the matrix species also include completely oxidized (i.e., lights out) species LO. This species LO, which is a derivative of the base glucose-indicator BA, has been photobleached and may not emit fluorescence.

The fluorescence $[I_{distortion}]$ from all the distortion-producing species is:

$$[I_{distortion}] = [Ox] + [Th] + [PA] \quad (8)$$

where [Ox], [PA], and [Th] are fluorescence from the oxidated species Ox, photo-activated oxidated species PA, and thermal degradation product species Th, respectively.

When the sensor is new (e.g., at manufacturing), the distortion producing subspecies (e.g., Ox, Th, and PA) of the indicator molecules 104 have not yet formed and may contribute nothing significant to the initial raw signal at turn-on. However, the distortion $I_{distortion}$ may increase from the time the sensor 100 is inserted in vivo. In particular, once the sensor 100 is inserted in vivo, the distortion producing subspecies (e.g., Ox, Th, and PA) may form progressively. Accordingly, in some embodiments, the circuitry of the sensor 100 may kinetically track the distortion-producing species (e.g., by using the tracked implant time $t_i$).

In some embodiments, the circuitry of sensor 100 (e.g., measurement controller 532) may compensate for the distortion $I_{distortion}$ present in the raw signal by calculating the fluorescence emitted from one or more of the distortion producing species (e.g., Ox, Th, and PA) and removing (e.g., subtracting) the non-glucose modulated fluorescence $I_{distortion}$ from the raw signal. For example, in embodiments where the raw signal is temperature corrected, the calculated non-glucose modulated fluorescence $I_{distortion}$ may be removed from the raw signal by subtracting the calculated distortion $I_{distortion}$ may be from the temperature corrected raw signal $[Signal]_T$.

In one non-limiting embodiment, the circuitry of the sensor 100 (e.g., measurement controller 532) may calculate the fluorescence emitted from one or more of the distortion producing species (e.g., oxidated species Ox, photo-activated oxidated species PA, and thermal degradation product species Th) as shown in equations 9-11:

$$[OX] = I_{0,QC} \% F_{Ox}[(1-e^{-k_{ox}t_{ox}})e^{-k_{th}t_{th}}e^{-k_{pb}t_{pb}}e^{-k_{pa}t_{pb}}] \\ [1-(T-37)c_{OX}] \quad (9)$$

$$[Th] = I_{0,QC} \% F_{Th}[(1-e^{-k_{th}t_{th}})e^{-k_{pb}t_{pb}}][1-(T-37)c_{Th}] \quad (10)$$

$$[PA] = I_{0,QC} \% F_{PA}[(1-e^{-k_{ox}t_{ox}})e^{-k_{th}t_{th}}e^{-k_{pb}t_{pb}} \\ (1-e^{-k_{pa}t_{pb}})][1-(T-37)c_{PA}] \quad (11)$$

where $I_{0,QC}$ is the fluorescence intensity of the base glucose indicator at zero glucose concentration $I_0$ obtained from manufacturing quality control (QC); $\%F_{Ox}$, $\%F_{Th}$, and $\%F_{PA}$ are the relative quantum efficiencies of Ox, Th, and PA, respectively, to the base glucose indicator BA; $k_{ox}$, $k_{th}$, and $k_{pb}$ are rates for oxidation, thermal degradation, and photobleaching, respectively; $t_{ox}$, $t_{th}$, and $t_{pb}$ are oxidation time, thermal degradation time, and photobleaching time, respectively; and $c_{Ox}$, $c_{Th}$, and $c_{PA}$ are the temperature correction coefficients of Ox, Th and PA, respectively. In some embodiments, the circuitry of the sensor 100 (e.g., measurement controller 532) may use the tracked cumulative emission time $t_e$ for the photobleaching time $t_{pb}$. In some embodiments, the circuitry of the sensor 100 may use the tracked implant time $t_i$ for the oxidation time $t_{ox}$ and thermal degradation time $t_{th}$.

The process 200 may include a step S218 of normalizing the raw signal, which in some embodiments may have be temperature corrected, offset compensated, and/or distortion compensated, into a normalized signal Sn. In some embodiments, the normalized signal Sn may be directly proportional to glucose concentration.

In its simplest form, the normalized signal Sn may be represented by the following equation:

$$Sn = \frac{I}{I_0} \quad (12)$$

where I is the glucose-modulated fluorescence from the indicator molecules 104 and $I_0$ is baseline glucose-modulated fluorescence at zero glucose concentration.

As explained above, only the glucose-modulated fluorescence I carries glucose concentration information, but the raw signal generated by the photodetector affected by temperature sensitivity and additionally contains an offset Z and a non-glucose modulated signal $I_{distortion}$. The raw signal may be corrected for temperature sensitivity and the offset Z and a non-glucose modulated signal $I_{distortion}$ may be removed, and, accordingly, the normalized signal Sn is may be represented by the following equation:

$$Sn = \frac{[Signal]_T - Z - I_{distortion}}{I_0} \quad (13)$$

where $[Signal]_T$ is the temperature corrected raw signal.

The circuitry of the sensor 100 (e.g., measurement controller 532) may remove noise from the raw signal and normalize it so that the normalized signal Sn may have a constant value at infinite glucose concentration. In other words, the normalized signal at infinite glucose concentration ($Sn_{max}$) may not change even the indicator molecules 104 are photobleached, oxidate, and thermally degrade. If the noise were not removed, the noise may compress the modulation shown in FIG. 5 (i.e., the Y-axis displacement from zero to infinite glucose), and the extent to which the modulation were compressed may change based on the extent to which the indicator molecules 104 were photobleached, oxidated, and/or thermally degraded.

In some embodiments, the circuitry of sensor 100 (e.g., measurement controller 532) may normalize the glucose-modulated fluorescence I by calculating the baseline glucose-modulated fluorescence at zero glucose concentration (i.e., $I_0$) and dividing the glucose-modulated fluorescence I by the calculated $I_0$.

In one non-limiting embodiment, the circuitry of the sensor 100 may calculate the baseline glucose-modulated fluorescence at zero glucose concentration $I_0$ according to the following equation:

$$I_0 = I_{0,QC} e^{-k_{ox}t_{ox}} e^{-k_{th}t_{th}} e^{-k_{pb}t_{pb}}[1-(T-37)c_f] \quad (14)$$

where $I_{0,QC}$ is the $I_0$ obtained from manufacturing quality control (QC); $e^{-k_{ox}t_{ox}}e^{-k_{th}t_{th}}e^{-k_{pb}t_{pb}}$ is the glucose indicator decay due to the superimposition of oxidation, thermal degradation, and photobleaching; $k_{ox}$, $k_{th}$, and $k_{pb}$ are rates for oxidation, thermal degradation and photobleaching, respectively; $t_{ox}$, $t_{th}$, and $t_{pb}$ are oxidation time, thermal degradation time, and photobleaching time, respectively; $c_f$ is the temperature correction coefficient of the glucose indicator; and T is the temperature of the optical sensor 100, which may be measured by the temperature sensor 670 in step S210. In some embodiments, the circuitry of the sensor 100 may use the tracked cumulative emission time $t_e$ for the photobleaching time $t_{pb}$. In some embodiments, the circuitry of the sensor 100 (e.g., measurement controller 532) may use the tracked implant time $t_i$ for the oxidation time $t_o$ and thermal degradation time $t_{th}$. The circuitry of the sensor 100 may be configured to kinetically track the first order decay loss of signal that occurs over time (e.g., by using the tracked cumulative emission time $t_e$ and tracked implant time $t_i$).

Figure 5:
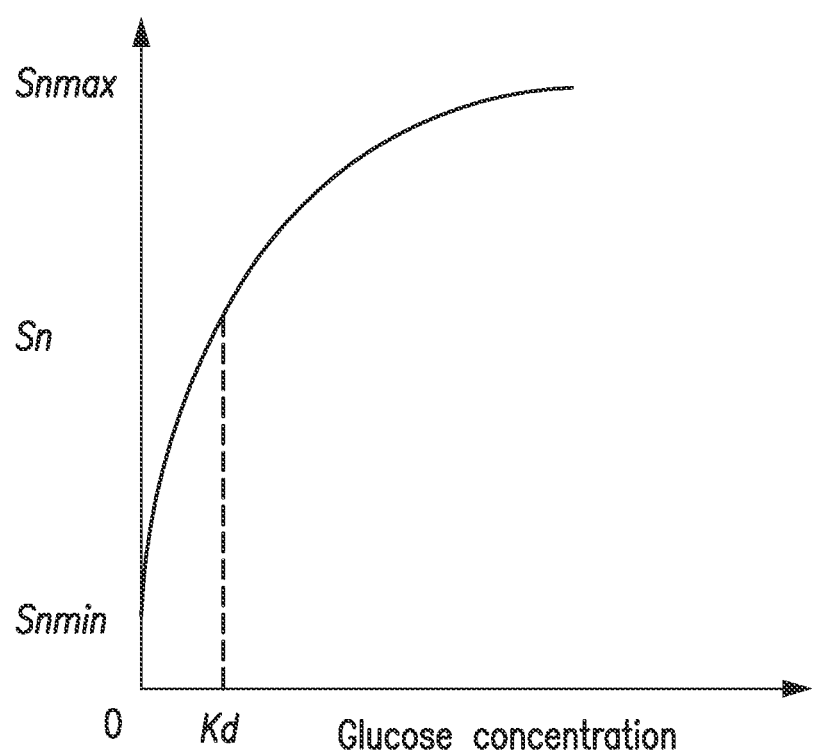
FIG. 5 illustrates the relationship between normalized glucose-modulated fluorescence ($I/I_0$) and glucose concentration in accordance with an embodiment of the present invention.

The process 200 may include a step S220 of converting the normalized signal Sn to a glucose concentration. The conversion of the normalized signal Sn into a glucose concentration may be based on the relationship between percent modulation and glucose as shown in FIG. 5. As described above, the percent modulation $I/I_0$ versus glucose concentration may be constant throughout the life of the glucose sensor 100. The end of life of the glucose sensor 100 may arise when the signal to noise ratio declines over time to a point where the error specification can no longer be maintained.

In some embodiments, the circuitry may use an interpretive algorithm to convert the normalized signal Sn into glucose concentration. The interpretive algorithm may be derived through a standard curve based on the following reaction:

$$A+B \leftrightarrow BA \tag{15}$$

where A is glucose indicator, B is glucose, and BA is glucose-indicator complex. The fluorescence of the indicator increases upon binding glucose.

The equilibrium expression for the dissociation defining $Sn_{max}$ (i.e., the normalized signal Ns at infinite glucose concentration) is $$K_d = \frac{[A][B]}{[AB]} \tag{16}$$

The glucose concentration [A] is $$[A] = K_d \frac{[AB]}{[B]} \tag{17}$$

where $K_d$ is constant, and [AB] and [B] terms must be determined from measurement. The following derivation illustrates how the glucose concentration [A] may be calculated at any one measurement (e.g., for any normalized signal Sn) based on the relationship shown in equations 16 and 17.

The total fluorescence F emitted by the indicator molecules 104 is:

$$F = F_B + F_{AB} \tag{18}$$

where $F_B$ is the fluorescence from the unbound indicator, and $F_{AB}$ is the fluorescence from the glucose indicator complex.

According to Beer's law:

$$F = I_e e b c \phi \tag{19}$$

where F is fluorescence of the species, $I_e$ is excitation light, e is molar extinction coefficient, b is path length, c is concentration of the fluorescer, and $\Phi$ is quantum efficiency.

By substituting specifically for the concentration terms for each of the glucose indicator A and the glucose-indicator complex AB, the fluorescence F is:

$$F = I_0 e b [B] \phi_B + I_0 e b [AB] \phi_{AB} \tag{20}$$

By defining:

$$q_B = \phi_B([B] + [AB]) \tag{21}$$

$$q_{AB} = \phi_{AB}([B] + [AB]) \tag{22}$$

$$f_B = \frac{[B]}{[B] + [AB]} \tag{23}$$

$$f_{AB} = \frac{[AB]}{[B] + [AB]} \tag{24}$$

equation (20) becomes:

$$F = I_e e b (f_B q_B + f_{AB} q_{AB}) \tag{25}$$

The fluorescent signal value at zero glucose concentration $F_{min}$, which is the lowest fluorescent signal value from the sensor, is:

$$F_{min} = I_e e b q_B \tag{26}$$

The opposite boundary condition occurs when glucose concentration is very high, almost all (e.g., 99.99%) of fluorescence signal is from the glucose indicator complex AB, and almost none (e.g., approaching zero) of the fluorescence signal is from unbound indicator B. The fluorescent signal value at glucose saturation $F_{max}$, which is the highest possible value of fluorescence, is:

$$F_{max} = I_e e b q_{AB} \tag{27}$$

By incorporating the equations for $F_{min}$ and $F_{max}$ (i.e., equations 26 and 27) into equation 25, equation 25 becomes $$F = F_{min} f_B + F_{max} f_{AB} = F_{min} f_B + F_{max}(1 - f_B) \tag{28}$$

Therefore, $$f_B = \frac{F_{max} - F}{F_{max} - F_{min}} \tag{29}$$

and $$f_{AB} = 1 - f_B = \frac{F - F_{min}}{F_{max} - F_{min}} \tag{30}$$

The glucose concentration [A] is:

$$[A] = K_d \frac{[AB]}{[B]} = K_d \frac{f_{AB}}{f_B} = K_d \frac{F - F_{min}}{F_{max} - F} \tag{31}$$

By substituting the normalized fluorescence Sn determined by the circuitry of the sensor 100 for the fluorescence F, the glucose concentration [A] becomes:

$$[A] = K_d \frac{Sn - Sn_{min}}{Sn_{max} - Sn} \tag{32}$$

where the dissociation constant $K_d$ and normalized signal at glucose saturation $Sn_{max}$ may be determined during manufacturing, the normalized signal Sn is generated by the circuitry of the sensor 100 by processing the raw signal generated by the photodetector of the sensor 100, and $Sn_{min}$ (i.e., $I_0/I_0$) is equal to one.

The process 200 may include the step S222 of conveying the glucose concentration to the external sensor reader 101. In some embodiments, the glucose concentration may be conveyed using the inductive element 114 of the sensor 100.

According to some embodiments of the invention, during sensor manufacturing, one or more sensors 100 may be cycled through a computer automated quality control measurement system. This system may measure parameters (e.g., $c_z$, $K_d$, $Sn_{max}$, $Z_{gel}$, $Z_{bleed}$). The cycle may include operating newly manufactured sensor 100 at two different temperatures (e.g., 32° C. and 37° C.) at three different glucose concentrations (e.g., 0 mM, 4.0 mM, and 18.0 mM glucose). The automated system may track the performance of each sensor 100 under these changing conditions and make specific measurements for each sequential temperature and concentration test. In some embodiments, other parameters (e.g., $K_{pb}$, $K_{pa}$, $K_{th}$, $\phi_z$, $c_f$, $c_{Th}$, $c_{ox}$, $c_{PA}$, % $F_{Ox}$, % $F_{PA}$ and % $F_{Th}$) may be developed from designed and controlled in vitro experiments, and still other parameters (e.g., $K_{Ox}$) may be developed from in vivo tests. One or more parameter values may be determined for each manufactured sensor 100 and used by the circuitry of the sensor 100 in processing a raw signal and converting the normalized signal Sn to a glucose concentration (e.g., according to the corresponding serial number of the sensor 100).

Figure 7:
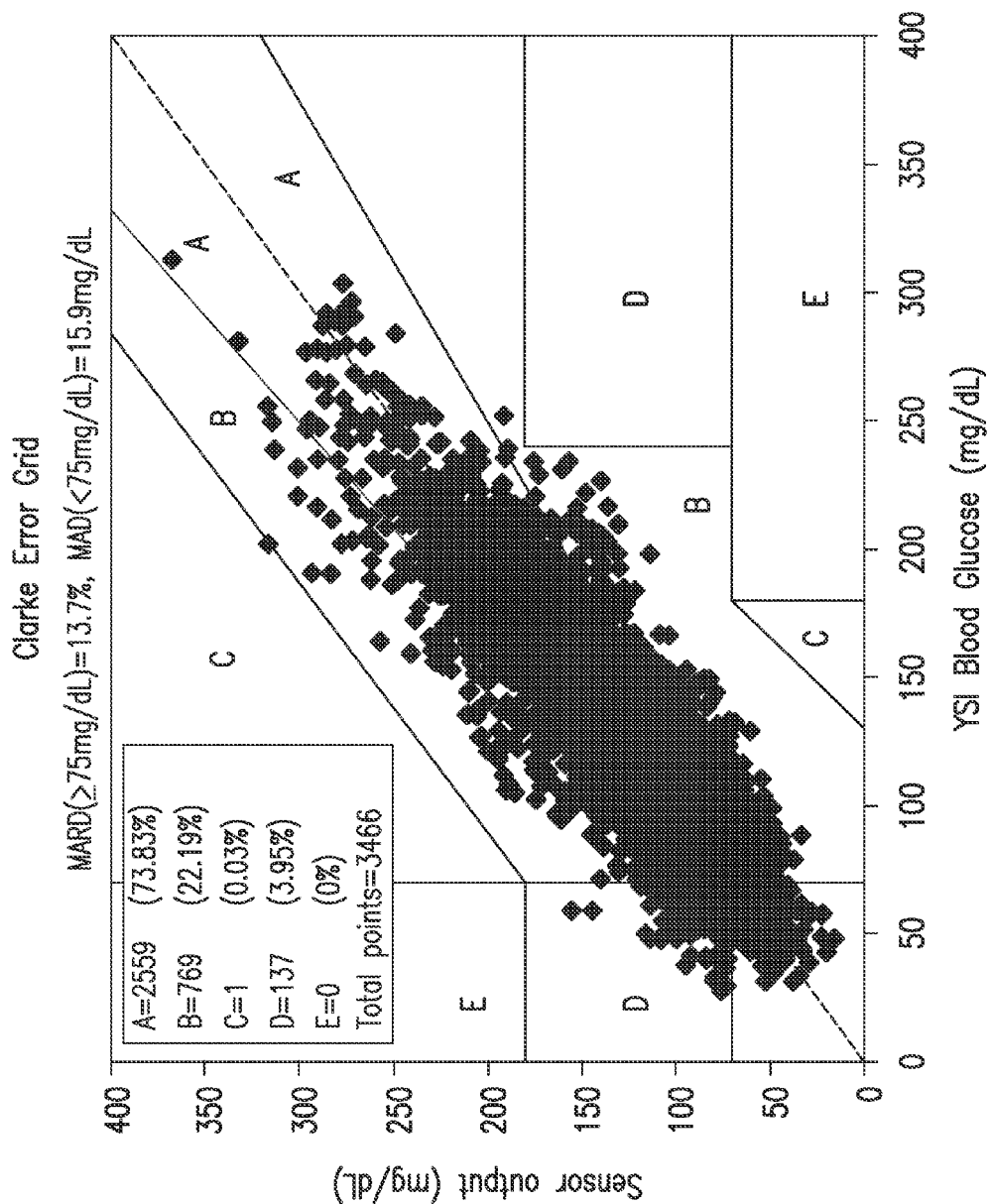
FIG. 7 illustrates a Clarke error grid showing the experimental results of 18 sensors embodying aspects of the present invention and implanted in Type I diabetic subjects.
Figure 8:
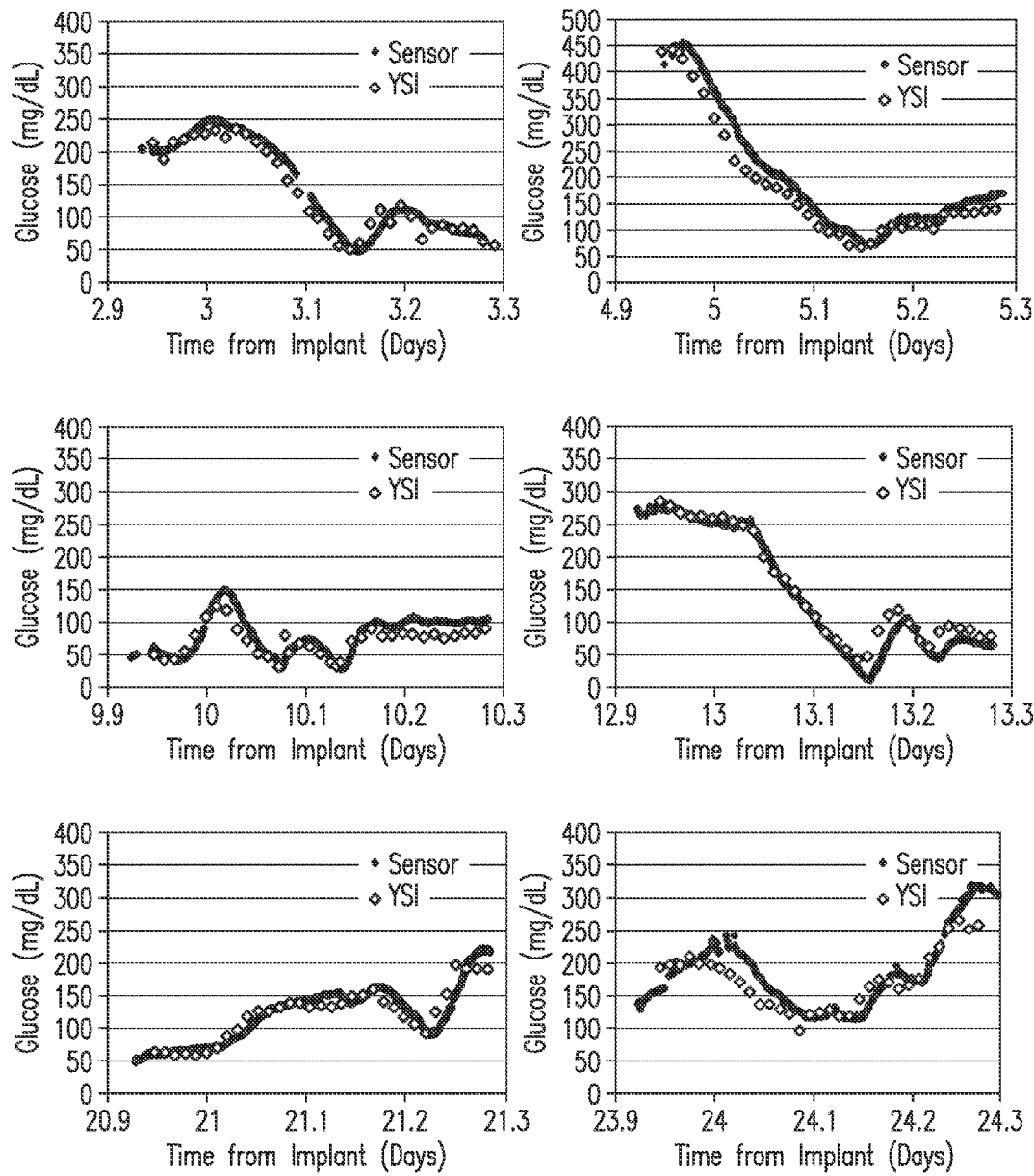
FIG. 8 illustrates experimental results of a sensor embodying aspects of the present invention during six read sessions.

In a non-limiting example of sensors that may be used to determine a concentration of glucose in a medium, experimental results were obtained using eighteen sensors incorporating one or more aspects of the present invention and implanted into type-I diabetic subjects. Data was collected during 6 in-clinic sessions to determine the sensor performance and the accuracy of the algorithm in vivo. The sensors were removed 28 days after insertion. The Mean Absolute Relative Difference (MARD) for all the 18 sensors from day 3 data collection through day 28 is 13.7%. Day 0 data collection was excluded as, in some embodiments, the sensor may not be fully responsive to glucose during a heal-up period. A total of 3,466 paired data points were obtained to evaluate sensor performance, and blood glucose measured by YSI machine was used as a reference. FIG. 7 is a Clarke error grid showing the 3,466 paired data points with 3328 data points (96.02%) in either the A range (i.e., values within 20% of the reference sensor) or the B range (i.e., values outside of 20% range but that may not lead to inappropriate treatment). FIG. 8 illustrates experimental results of a sensor embodying aspects of the present invention during six read sessions. FIG. 8 shows the performance of one of the implanted sensors during the six read sessions and shows that the sensor tracks the blood glucose well. The MARD for this sensor is 13%. Other embodiments of the sensor may be used to produce different results.

In some embodiments, as described above, the circuitry of the sensor 100 (which may, for example, include measurement controller 532) may eliminate noise (e.g., offset and distortions) present in the raw signal generated by the photodetector 224 and convert the purified raw signal into a glucose concentration, and the sensor 100 may convey the glucose concentration to the sensor reader 101. However, this is not required, and, in alternative embodiments, the sensor 100 may convey the raw signal generated by the photodetector 224 to the sensor reader 101, and circuitry of the sensor reader 101 (which may, for example, include PIC microcontroller 920) may eliminate noise present in the raw signal generated by the photodetector 224 and convert the purified raw signal into a glucose concentration. For example, in some embodiments, the circuitry of the sensor reader 101 may (i) purify the raw signal, (ii) normalize the purified signal to produce a normalized signal Sn that is directly proportional to glucose concentration, and (iii) convert the normalized signal Sn into a glucose concentration.

Figure 10:
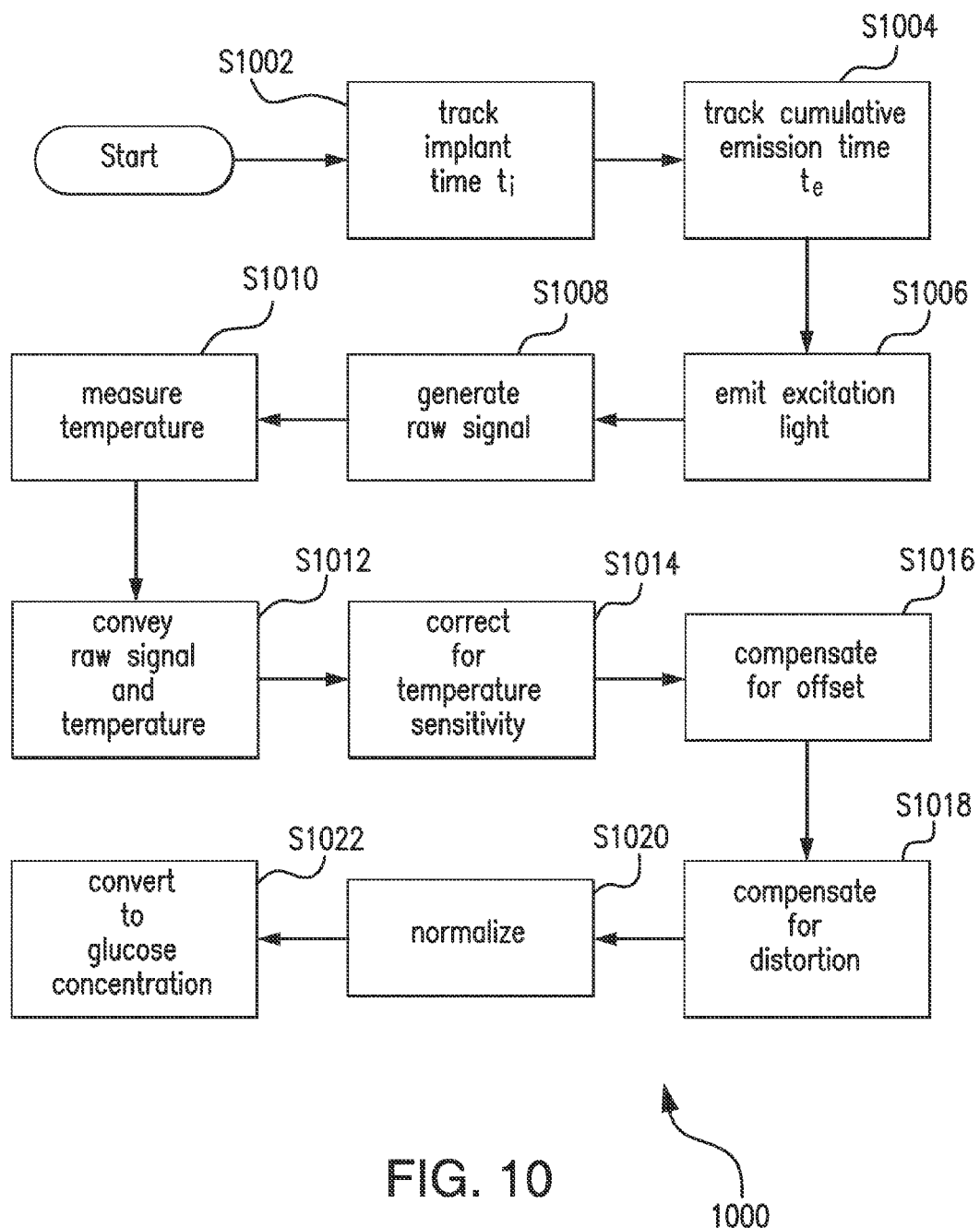
FIG. 10 illustrates a raw signal purification and conversion process that may be performed by the circuitry of a sensor reader in accordance with an embodiment of the present invention.

FIG. 10 illustrates an exemplary raw signal purification and conversion process 1000 that may be performed by a system including the sensor 100, which may be, for example, implanted within a living animal (e.g., a living human), and a sensor reader 101, which may be external to the living animal but in the proximity of the sensor 100 (e.g., on an armband or wristband attached to the living animal), in accordance with an embodiment of the present invention. The process 1000 may include a step S1002 of tracking the amount of time $t_i$ that has elapsed since the optical sensor 100 was implanted in the living animal. As noted above, because oxidation and thermal degradation begins when the sensor 100 is implanted, the implant time $t_i$ may be equivalent to the oxidation time $t_o$ and the thermal degradation time $t_{th}$.

In some embodiments, the circuitry of sensor reader 101 may include an implant timer circuit that is started when the sensor 100 is implanted. For example, in one non-limiting embodiment, the implant timer circuit may be a counter that increments with each passing of a unit of time (e.g., one or more milliseconds, one more seconds, one or more minutes, one or more hours, or one or more days, etc.). However, this is not required, and, in some alternative embodiments, the circuitry of the sensor reader 101 may track the implant time $t_i$ by storing the time at which the sensor 100 was implanted (e.g., in memory 922) and comparing the stored time with the current time. In other alternative embodiments, the sensor 100 may receive the time at which the sensor was implanted, i.e., the implant time from the sensor reader 101 (e.g., when the sensor 100 and sensor reader 101 are first linked together) and store the received implant time $t_i$ (e.g., in nonvolatile storage medium 660). The sensor reader 101 may receive the time at which sensor 100 was implanted from the sensor 100 for calculation of the implant time $t_i$. The tracked implant time $t_i$ may be used in compensating for distortion in the raw signal, normalizing the raw signal, and/or converting the normalized signal Sn to a glucose concentration.

The process 1000 may include a step S1004 of tracking the cumulative amount of time $t_e$ that the light source 108 has emitted the excitation light 329. Because the indicator molecules 104 are irradiated with the excitation light 329, the cumulative emission time $t_e$ may be equivalent to the photobleaching time $t_{pb}$.

In some embodiments, the circuitry of sensor 100 may include an emission timer circuit that is advanced while the light source 108 emits excitation light 329. For example, in one non-limiting embodiment, the emission timer circuit may be a counter that increments with each passing of a unit of time (e.g., one or more milliseconds, one more seconds, one or more minutes, one or more hours, or one or more days, etc.) while the light source 108 emits excitation light 329. The count may be conveyed by the sensor 100 to the sensor reader 101. However, this is not required. For example, in some alternative embodiments, the light source 108 may emit excitation light 329 for a set amount of time for each measurement, and the counter may increment once for each measurement taken by the sensor 100. Here again, the count may be conveyed by the sensor 100 to the sensor reader 101. In another alternative embodiment, the light source 108 may emit excitation light 329 for a set amount of time for each measurement, and the circuitry of the sensor reader 101 may include an emission timer circuit that is incremented once for each measurement command issued by the sensor reader 101 to the sensor 100 or for each measurement received by the sensor reader 101 from the sensor 100. The tracked cumulative emission time $t_e$ may be used in compensating for offset in the raw signal, compensating for distortion in the raw signal, normalizing the raw signal, and/or converting the normalized signal Sn to a glucose concentration.

The process 1000 may include a step S1006 of emitting excitation light 329, a step S208 of generating a raw signal indicative of the amount of light received by a photodetector, and/or a step S1010 of measuring the temperature T of the optical sensor 100, which may correspond to steps S206, S208, and S210, respectively, of the process 200 described above with reference to FIG. 2.

The process 1000 may include a step S1012 of conveying the raw signal indicative of the amount of light received by a photodetector, which may be a digitized raw signal, and/or the measured temperature. In some embodiments, the raw signal and/or measured temperature may be conveyed using the inductive element 114 of the sensor 100. The sensor reader 101 may receive the conveyed raw signal and/or measured temperature (e.g., using the inductive element 103 of the sensor reader 101).

The process 1000 may include a step S1014 of temperature correcting the raw signal based on the measured temperature of the sensor 100, a step S1016 of compensating for the offset Z present in the raw signal, a step S1018 of compensating for the distortion $I_{distortion}$ present in the raw signal, a step S1020 of normalizing the raw signal, and a step S1022 of converting the normalized signal Sn to a glucose concentration. These steps may correspond to steps S212, S214, S216, S218, and S220, respectively, of the process 200 described above with reference to FIG. 2, except that steps S1014, S1016, S1018, S1020, and S1022 may be performed the circuitry of the sensor reader 101 (e.g., by the PIC microcontroller 920) instead of by the circuitry of the sensor 100 (e.g., by measurement controller 532).

In some embodiments, the sensor reader 101 may store (e.g., in memory 922) parameters specific to the sensor 100 and use the parameters during performance of steps S1014, S1016, S1018, S1020, and/or S1022. In some non-limiting embodiments, the sensor reader 101 may download some or all of the parameters specific to the sensor 100 from a web server. In some non-limiting embodiments, the sensor reader 101 may receive some or all of the parameters specific to the sensor 100 from the sensor 100, which may store the parameters (e.g., in nonvolatile storage medium 660) and convey the parameters to the sensor reader 101 (e.g., using inductive element 114). In some embodiments, the parameters specific to the sensor 100 may include static parameters and/or dynamic parameters. For instance, in some non-limiting embodiments, the parameters specific to the sensor 100 may include static sensor parameters (e.g., $K_{pb}$, $K_{pa}$, $K_{th}$, $\phi_z$, $c_f$, $c_{Th}$, $c_{ox}$, $c_{PA}$, % $F_{Ox}$, % $F_{PA}$ and/or % $F_{Th}$) developed from controlled in vitro experiments and/or static sensor parameters (e.g., $K_{Ox}$) developed from in vivo tests. In some non-limiting embodiments, the sensor reader 101 may store parameters for only one sensor 100 at a time and be paired to a particular sensor 100 after receiving the sensor's parameters (e.g., by downloading them from a web server or receiving them from the sensor 100). However, in alternative embodiments, the sensor reader 101 may store parameters for more than one sensor 100. For example, in one non-limiting embodiment, the sensor reader 101 may store parameters for all of the sensors 100 with which the sensor reader 101 may be used.

In another alternative embodiment, the circuitry of the sensor 100 (which may, for example, include measurement controller 532) may eliminate noise (e.g., temperature sensitivity, offset, and distortions) present in the raw signal generated by the photodetector 224, the sensor 100 may convey the purified raw signal to the sensor reader 101, and the sensor reader 101 may convert the purified raw signal into a glucose concentration.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For example, the circuitry of the sensor 100 and/or the sensor reader 101 may be implemented in hardware, software, or a combination of hardware and software. The software may be implemented as computer executable instructions that, when executed by a processor, cause the processor to perform one or more functions.

What is claimed is:

1. A method of determining a concentration of glucose in a medium of a living animal using an optical sensor implanted in the living animal and a sensor reader external to the living animal, the method comprising:
   emitting, using a light source of the optical sensor, excitation light to indicator molecules of the optical sensor, the indicator molecules having an optical characteristic responsive to the concentration of glucose;
   generating, using a photodetector of the optical sensor, a raw signal indicative of the amount of light received by the photodetector, wherein the light received by the photodetector includes glucose-modulated light emitted by the indicator molecules and at least one of excitation light emitted by the light source and non-glucose modulated light emitted by the indicator molecules;
   conveying, using an inductive element of the optical sensor, the raw signal;
   receiving, using an inductive element of the sensor reader, the conveyed raw signal;
   tracking, using circuitry of the sensor reader, the cumulative emission time that the light source has emitted the excitation light;
   tracking, using circuitry of the sensor reader, the implant time that has elapsed since the optical sensor was implanted in the living animal;
   adjusting, using circuitry of the sensor reader, the received raw signal to compensate for offset and distortion based on the tracked cumulative emission time and the tracked implant time; and
   converting, using circuitry of the sensor reader, the adjusted signal into a measurement of glucose concentration in the medium of the living animal.

2. The method of claim 1, further comprising:
   measuring, using a temperature sensor of the optical sensor, a temperature of the optical sensor;
   conveying, using the inductive element of the optical sensor, the measured temperature of the optical sensor;
   receiving, using the inductive element of the sensor reader, the conveyed temperature of the optical sensor;
   correcting, using circuitry of the sensor reader, the received raw signal indicative of the amount of light received by the photodetector to compensate for temperature sensitivity of the light source based on the received temperature.

3. The method of claim 1, wherein the non-glucose modulated light emitted by the indicator molecules comprises light emitted by distortion producing indicator molecule subspecies.

4. The method of claim 3, wherein the distortion producing indicator molecule subspecies include oxidated species, and adjusting the received raw signal comprises:
   calculating the light emitted by the oxidated species based on the tracked cumulative emission time and the tracked implant time; and
   subtracting the calculated light emitted by the oxidated species from the received raw signal.

5. The method of claim 4, wherein the distortion producing indicator molecule subspecies include photo-activated oxidated species, and adjusting the received raw signal comprises:
   calculating the light emitted by the photo-activated oxidated species based on the tracked cumulative emission time and the tracked implant time; and
   subtracting the calculated light emitted by the photo-activated oxidated species from the received raw signal.

6. The method of claim 3, wherein the distortion producing indicator molecule subspecies include then tal degradation product species, and adjusting the received raw signal comprises:
   calculating the light emitted by the thermal degradation product species based on the tracked cumulative emission time and the tracked implant time; and subtracting the calculated light emitted by the thermal degradation product species from the received raw signal.

7. The method of claim 1, wherein the offset is hardware based, and adjusting the received raw signal comprises:
   calculating the offset based on the tracked cumulative emission time; and
   subtracting the calculated offset from the received raw signal.

8. The method of claim 1, wherein the adjusted signal is directly proportional to glucose concentration in the medium.

9. The method of claim 1, wherein the glucose-modulated light is emitted by active indicator species of the indicator molecules.

10. The method of claim 9, wherein adjusting the received raw signal comprises normalizing the received raw signal to a normalized raw signal that would be equal to one at zero glucose concentration.

11. The method of claim 10, wherein normalizing comprises:
    calculating the amount of light emitted by the active indicator species at zero glucose concentration based on the tracked cumulative emission time and the tracked implant time; and
    dividing the received raw signal by the calculated amount of light emitted by the active indicator species at zero glucose concentration.

12. The method of claim 10, further comprising:
    measuring, using a temperature sensor of the optical sensor, a temperature of the optical sensor;
    conveying, using the inductive element of the optical sensor, the measured temperature of the optical sensor; and
    receiving, using the inductive element of the sensor reader, the conveyed temperature of the optical sensor;
    wherein calculating the amount of light emitted by the active indicator species at zero glucose concentration is based on the received temperature, the tracked cumulative emission time, and the tracked implant time.

13. The method of claim 1, wherein the non-glucose modulated light is emitted by oxidated species, photo-activated oxidated species, and/or photo-activated oxidated species of the indicator molecules.

14. A system for determining a concentration of glucose in a medium of a living animal, the system comprising:
    (1) an optical sensor configured to be implanted in the living animal, wherein the optical sensor includes:
       (a) indicator molecules having an optical characteristic responsive to the concentration of glucose;
       (b) a light source configured to emit excitation light to the indicator molecules;
       (c) a photodetector configured to generate a raw signal indicative of the amount of light received by the photodetector, wherein the light received by the photodetector includes glucose-modulated light emitted by the indicator molecules and at least one of excitation light emitted by the light source and non-glucose modulated light emitted by the indicator molecules; and
       (d) an inductive element configured to convey the raw signal; and
    (2) an external sensor reader, the sensor reader including:
       (a) an inductive element configured to receive the conveyed raw signal; and
       (b) circuitry configured to:
          (i) track the cumulative emission time that the light source has emitted the excitation light;
          (ii) track the implant time that has elapsed since the optical sensor was implanted in the living animal;
          (iii) adjust the received raw signal to compensate for offset and distortion based on the tracked cumulative emission time and the tracked implant time; and
          (iv) convert the adjusted signal into a measurement of glucose concentration in the medium of the living animal.

15. The system of claim 14, wherein the optical sensor further comprises a temperature sensor configured to measure a temperature of the optical sensor;
    wherein the inductive element of the optical sensor is configured to convey the measured temperature of the optical sensor, the inductive element of the sensor reader is configured to receive the conveyed temperature, and the circuitry of the sensor reader is further configured to correct the received raw signal to compensate for temperature sensitivity of the light source based on the received temperature.

16. The system of claim 14, wherein the circuitry is further configured to normalize the received raw signal to a normalized raw signal that would be equal to one at zero glucose concentration.

17. The system of claim 14, wherein the optical sensor includes (e) circuitry configured to convert the raw signal into a digital raw signal, and the conveyed raw signal is the digital raw signal.

18. A method of determining a concentration of glucose in a medium of a living animal using an optical sensor implanted in the living animal and a sensor reader external to the living animal, the method comprising:
    emitting, using a light source of the optical sensor, excitation light to indicator molecules of the optical sensor, the indicator molecules having an optical characteristic responsive to the concentration of glucose;
    generating, using a photodetector of the optical sensor, a raw signal indicative of the amount of light received by the photodetector, wherein the light received by the photodetector includes glucose-modulated light emitted by the indicator molecules and at least one of excitation light emitted by the light source and non-glucose modulated light emitted by the indicator molecules;
    measuring, using a temperature sensor of the optical sensor, a temperature of the optical sensor;
    conveying, using an inductive element of the optical sensor, the raw signal and the measured temperature;
    receiving, using an inductive element of the sensor reader, the conveyed raw signal and the conveyed temperature;
    tracking the cumulative emission time that the light source has emitted the excitation light;
    tracking the implant time that has elapsed since the optical sensor was implanted in the living animal;
    temperature correcting, using circuitry of the sensor reader, the received raw signal to compensate for temperature sensitivity of the light source based on the received temperature;
    offset adjusting, using the circuitry of the sensor reader, the temperature corrected raw signal to compensate for offset based on the tracked cumulative emission time;
    distortion adjusting, using the circuitry of the sensor reader, the offset adjusted raw signal to compensate for distortion based on the tracked cumulative emission time and the tracked implant time;
    normalizing, using the circuitry of the sensor reader, the distortion adjusted raw signal to a normalized raw signal that would be equal to one at zero glucose concentration based on the measured temperature, the tracked cumulative emission time, and the tracked implant time; and converting, using the circuitry of the sensor reader, the normalized raw signal into a measurement of glucose concentration in the medium of the living animal.

19. A method of determining a concentration of glucose in a medium of a living animal using an optical sensor implanted in the living animal and a sensor reader external to the living animal, the method comprising:
   emitting, using a light source of the optical sensor, excitation light to indicator molecules of the optical sensor, the indicator molecules having an optical characteristic responsive to the concentration of glucose;
   generating, using a photodetector of the optical sensor, a raw signal indicative of the amount of light received by the photodetector, wherein the light received by the photodetector includes glucose-modulated light emitted by the indicator molecules and at least one of excitation light emitted by the light source and non-glucose modulated light emitted by the indicator molecules;
   tracking the cumulative emission time that the light source has emitted the excitation light;
   tracking the implant time that has elapsed since the optical sensor was implanted in the living animal;
   adjusting the raw signal to compensate for offset and distortion based on the tracked cumulative emission time and the tracked implant time; and
   converting the adjusted signal into a measurement of glucose concentration in the medium of the living animal.

20. The method of claim 19, further comprising:
   measuring, using a temperature sensor of the optical sensor, a temperature of the optical sensor; and
   correcting the raw signal to compensate for temperature sensitivity of the light source based on the received temperature.

21. The method of claim 19, wherein the non-glucose modulated light emitted by the indicator molecules comprises light emitted by distortion producing indicator molecule subspecies.

22. The method of claim 21, wherein the distortion producing indicator molecule subspecies include oxidated species, and adjusting the raw signal comprises:
   calculating the light emitted by the oxidated species based on the tracked cumulative emission time and the tracked implant time; and
   subtracting the calculated light emitted by the oxidated species from the raw signal.

23. The method of claim 22, wherein the distortion producing indicator molecule subspecies include photo-activated oxidated species, and adjusting the raw signal comprises:
   calculating the light emitted by the photo-activated oxidated species based on the tracked cumulative emission time and the tracked implant time; and
   subtracting the calculated light emitted by the photo-activated oxidated species from the raw signal.

24. The method of claim 21, wherein the distortion producing indicator molecule subspecies include thermal degradation product species, and adjusting the raw signal comprises:
   calculating the light emitted by the thermal degradation product species based on the tracked cumulative emission time and the tracked implant time; and
   subtracting the calculated light emitted by the thermal degradation product species from the raw signal.

25. The method of claim 19, wherein the offset is hardware based, and adjusting the raw signal comprises:
   calculating the offset based on the tracked cumulative emission time; and
   subtracting the calculated offset from the raw signal.

26. The method of claim 19, wherein the adjusted signal is directly proportional to glucose concentration in the medium.

27. The method of claim 19, wherein the glucose-modulated light is emitted by active indicator species of the indicator molecules.

28. The method of claim 27, wherein adjusting the raw signal comprises normalizing the signal to a normalized raw signal that would be equal to one at zero glucose concentration.

29. The method of claim 28, wherein normalizing comprises:
   calculating the amount of light emitted by the active indicator species at zero glucose concentration based on the tracked cumulative emission time and the tracked implant time; and
   dividing the raw signal by the calculated amount of light emitted by the active indicator species at zero glucose concentration.

30. The method of claim 28, further comprising measuring, using a temperature sensor of the optical sensor, a temperature of the optical sensor;
   wherein calculating the amount of light emitted by the active indicator species at zero glucose concentration is based on the received temperature, the tracked cumulative emission time, and the tracked implant time.

31. The method of claim 19, wherein the non-glucose modulated light is emitted by oxidated species, photo-activated oxidated species, and/or photo-activated oxidated species of the indicator molecules.

32. A method of determining a concentration of glucose in a medium of a living animal using an optical sensor implanted in the living animal and a sensor reader external to the living animal, the method comprising:
   emitting, using a light source of the optical sensor, excitation light to indicator molecules of the optical sensor, the indicator molecules having an optical characteristic responsive to the concentration of glucose;
   generating, using a photodetector of the optical sensor, a raw signal indicative of the amount of light received by the photodetector, wherein the light received by the photodetector includes glucose-modulated light emitted by the indicator molecules and at least one of excitation light emitted by the light source and non-glucose modulated light emitted by the indicator molecules;
   measuring, using a temperature sensor of the optical sensor, a temperature of the optical sensor;
   tracking the cumulative emission time that the light source has emitted the excitation light;
   tracking the implant time that has elapsed since the optical sensor was implanted in the living animal;
   temperature correcting the raw signal to compensate for temperature sensitivity of the light source based on the measured temperature;
   offset adjusting the temperature corrected raw signal to compensate for offset based on the tracked cumulative emission time;
   distortion adjusting the offset adjusted raw signal to compensate for distortion based on the tracked cumulative emission time and the tracked implant time;
   normalizing the distortion adjusted raw signal to a normalized raw signal that would be equal to one at zero glucose concentration based on the measured temperature, the tracked cumulative emission time, and the tracked implant time; and converting the normalized raw signal into a measurement of glucose concentration in the medium of the living animal.

\* \* \* \* \*